(12) United States Patent
Goldstein et al.

(10) Patent No.: US 6,576,632 B1
(45) Date of Patent: Jun. 10, 2003

(54) BIARYL COMPOUNDS USEFUL AS ANTICANCER AGENTS

(75) Inventors: Steven W. Goldstein, Noank, CT (US); Kelly P. Longo, Mystic, CT (US); James F. Blake, Mystic, CT (US); Mohamed M. A. Awad, Westerly, RI (US); Kenneth P. Raiche, Charlestown, RI (US); Kevin W. Kramer, Gales Ferry, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/548,460

(22) Filed: Apr. 13, 2000

Related U.S. Application Data
(60) Provisional application No. 60/151,139, filed on Aug. 27, 1999.

(51) Int. Cl.$^7$ ............... C07C 233/05; C07C 233/06; C07C 309/00; A61K 31/16; A61K 31/175
(52) U.S. Cl. ............... 514/242; 548/544; 548/227; 548/366.4; 548/132; 548/183; 548/317.1; 548/263.4; 548/251; 548/122; 548/255; 514/425; 514/429; 514/473; 514/376; 514/380; 514/364; 514/369; 514/392; 514/593; 514/600; 514/404; 514/384; 514/381; 514/360; 514/359; 549/313; 564/43; 564/95; 564/86; 564/171; 544/182
(58) Field of Search ............... 548/544, 227, 548/366.4, 132, 183, 317.1, 263.4, 251, 122, 255; 514/425, 429, 473, 376, 380, 364, 369, 392, 593, 600, 404, 384, 381, 360, 359, 242; 549/313; 564/43, 95, 86; 544/182

(56) References Cited

PUBLICATIONS

Springer et al. A simple synthesis of biaryl phospholipase A2 inhbitors, Bioorganic & Medicinal Chemistry, 22: 2669–2672, Apr. 1996.*

CAS printout for Kiely and Eyer, Feb. 1982.*

\* cited by examiner

*Primary Examiner*—Richard L. Raymond
*Assistant Examiner*—Hong Liu
(74) *Attorney, Agent, or Firm*—Peter C. Richardson; Paul H. Ginsburg; Krishna G. Banerjee

(57) ABSTRACT

The present invention relates to compounds of formula I

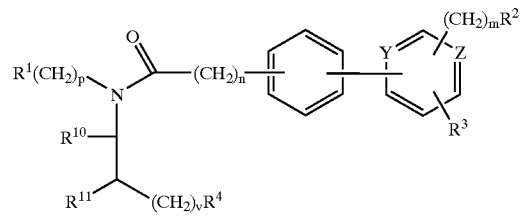

and to pharmaceutically acceptable salts, hydrates and prodrugs thereof, wherein $R^1$, $R^2$, $R^3$, $R^4$, $R^5$, $R^{10}$, $R^{11}$, b, m, n, p and v are as defined herein. The invention also relates to pharmaceutical compositions containing the above compounds and methods of treating hyperproliferative disorders in mammals by administering the above compounds.

6 Claims, No Drawings

BIARYL COMPOUNDS USEFUL AS ANTICANCER AGENTS

This application is based upon co-pending provisional application 60/151,139 filed Aug. 27, 1999.

BACKGROUND OF THE INVENTION

This invention relates to novel biaryl compounds that are useful in the treatment of hyperproliferative diseases, such as cancers, in mammals. This invention also relates to a method of using such compounds in the treatment of hyperproliferative diseases in mammals, especially humans, and to pharmaceutical compositions containing such compounds.

A cell may become cancerous by virtue of the transformation of a portion of its DNA into an oncogene (i.e. a gene that upon activation leads to the formation of malignant tumor cells). Many oncogenes encode proteins that are aberrant tyrosine kinases capable of causing cell transformation. Alternatively, the overexpression of a normal proto-oncogenic tyrosine kinase may also result in proliferative disorders, sometimes resulting in a malignant phenotype. It has been shown that certain tyrosine kinases may be mutated or overexpressed in many human cancers such as brain, lung, squamous cell, bladder, gastric, breast, head and neck, oesophageal, gynecological and thyroid cancers. Furthermore, the overexpression of a ligand for a tyrosine kinase receptor may result in an increase in the activation state of the receptor, resulting in proliferation of the tumor cells or endothelial cells. Thus, it is believed that the growth of mammalian cancer cells can be selectively inhibited by reducing tyrosine kinase activity.

Polypeptide growth factors, such as vascular endothelial growth factor (VEGF) having a high affinity to the human kinase insert-domain-containing receptor (KDR) or the murine fetal liver kinase 1 (FLK-1) receptor, have been associated with the proliferation of endothelial cells and more particularly vasculogenesis and angiogenesis. See PCT international application publication number WO 95/21613 (published Aug. 17, 1995). A significant body of evidence has been put forth detailing the importance of VEGF in the formation of new blood vessels (angiogenesis). It has also been noted that new blood vessel formation is crucial in supplying and maintaining the physiological conditions and nutrients necessary for tumor growth and metastasis. It has been shown that both VEGF receptor subtypes appear to be over expressed in proliferating endothelial cells located in near proximity to tumor cells in vivo. At the molecular level, intracellular portions of both FLT-1 and FLK-1 contain functional tyrosine kinase domains. Kinase activities depend on high affinity to, and interaction with, VEGF. Such interaction results in the autophosphorylation of the receptors and ultimately in endothelial cell proliferation. High affinity VEGF binding and the resulting functional effects appear to depend on the presence of specific heparin sulfate proteoglycans (VEGF glyceptor) associated with the extracellular matrix of endothelial cells. This supposition is supported by the ability of exogenous levels of heparin to inhibit VEGF induced endothelial cell proliferation by acting as a sink for secreted VEGF. By inhibiting the binding of VEGF to VEGF glyceptor (GAG), phosphorylation of tyrosine (kinase) is modulated. Agents, such as the compounds of the present invention, which are capable of modulating the KDR/FLK-1 receptor, may be used to treat disorders related to vasculogenesis or angiogenesis. Such disorders include, but are not limited to, diabetes, diabetic retinopathy, hemangioma, glioma, melanoma, Kaposi's sarcoma and ovarian, breast, lung, pancreatic, prostate, colon and epidermoid cancer.

SUMMARY OF THE INVENTION

The present invention relates to compounds of the formula I

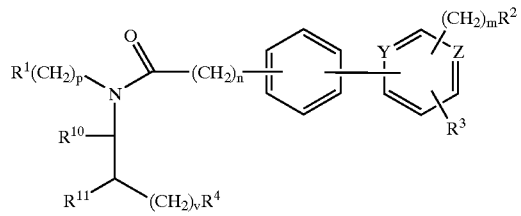

and to pharmaceutically acceptable salts, hydrates and prodrugs thereof, wherein:

$R^1$ is H, $C_1$–$C_{10}$ alkyl, $C_2$–$C_{10}$ alkenyl, $C_2$–$C_{10}$ alkynyl, —$(CH_2)_t(C_6$–$C_{10}$ aryl), or —$(CH_2)_t$(4 to 10 membered heterocyclic), wherein t is an integer from 0 to 5; said alkyl group optionally including 1 or 2 hetero moieties selected from O, S and —N($R^6$)— with the proviso that two O atoms, two S atoms, or an O and S atom are not attached directly to each other; said aryl and heterocyclic $R^1$ groups being optionally fused to a $C_6$–$C_{10}$ aryl group, a $C_5$–$C_8$ saturated cyclic group, or a 4 to 10 membered heterocyclic group; one or two carbon atoms in said 4 to 10 membered heterocyclic group of $R^1$ and $R^5$ being optionally substituted by an oxo (=O) moiety; the —$(CH_2)_t$— moieties of $R^1$ optionally including a carbon-carbon double or triple bond when t is an integer from two to five; $R^1$ groups being optionally substituted by one to five $R^5$ groups;

each $R^5$ is independently selected from $C_1$–$C_{10}$ alkyl, $C_2$–$C_{10}$ alkenyl, $C_2$–$C_{10}$ alkynyl, halo, cyano, nitro, trifluoromethyl, trifluoromethoxy, azido, —$OR^6$, —$C(O)R^7$, —$C(O)OR^6$, —$NR^7C(O)OR^6$, —$OC(O)R^6$, —$NR^7SO_2R^6$, —$SO_2NR^6R^7$, —$NR^7C(O)R^6$, —$C(O)NR^6R^7$, —$NR^6R^7$, —$S(O)_jR^8$ wherein j is an integer ranging from zero to two, —$SO_3H$, —$NR^6(CR^7R^8)_tOR^7$, —$(CH_2)_t(C_6$–$C_{10}$ aryl), —$SO_2(CH_2)_t(C_6$–$C_{10}$ aryl), —$S(CH_2)_t(C_6$–$C_{10}$ aryl), —$O(CH_2)_t(C_6$–$C_{10}$ aryl), —$(CH_2)_t$(4 to 10 membered heterocyclic), and —$(CR^7R^8)_mOR^7$, wherein m is an integer from one to five and t is an integer from zero to five; said alkyl group optionally containing one or two hetero moieties selected from O, S and —N($R^7$)— with the proviso that two O atoms, two S atoms, or an O and S atom are not attached directly to each other; aryl and heterocyclic moieties of $R^5$ being optionally fused to a $C_6$–$C_{10}$ aryl group, a $C_5$–$C_8$ saturated cyclic group, or a 4 to 10 membered heterocyclic group; one or two carbon atoms of the heterocyclic moieties of $R^5$ being optionally substituted by an oxo (=O) moiety; and the alkyl, aryl and heterocyclic moieties of $R^5$ groups being optionally substituted by one to three substituents independently selected from halo, cyano, nitro, trifluoromethyl, trifluoromethoxy, azido, —$NR^7SO_2R^6$, —$SO_2NR^6R^7$, —$C(O)R^6$, —$C(O)OR^6$, —$OC(O)R^6$, —$NR^7C(O)R^6$, —$C(O)NR^6R^7$, —$NR^6R^7$, —$(CR^7R^8)_mOR^7$ wherein m is an integer from one to five, —$OR^6$ and $R^6$;

each $R^6$ is independently selected from H, $C_1$–$C_{10}$ alkyl, —$(CH_2)_t(C_6$–$C_{10}$ aryl), and —$(CH_2)_t$(4 to 10 membered heterocyclic), wherein t is an integer from zero to five; said alkyl group optionally including one or two hetero moieties selected from O, S and —N($R^5$)— with the proviso that two O atoms, two S atoms, or an O and S atom are not attached directly to each other; said aryl and heterocyclic $R^6$ groups being optionally fused to a $C_6$–$C_{10}$ aryl group, a $C_5$–$C_8$ saturated cyclic group, or a 4 to 10 membered heterocyclic group; the foregoing moieties of $R^6$, with the exception of H, being optionally substituted by one to three substituents independently selected from halo, cyano, nitro, trifluoromethyl, trifluoromethoxy, azido, —C(O)$R^7$, —C(O)O$R^7$, —CO(O)$R^7$, —N$R^7$C(O)$R^8$, —C(O)N$R^7R^8$, —N$R^7R^8$, hydroxy, $C_1$–$C_6$ alkyl, and $C_1$–$C_6$ alkoxy;

each $R^7$ and $R^8$ is independently H or $C_1$–$C_6$ alkyl;

$R^2$ is a group having an acidic proton, particularly —CO$_2$H, —CONHSO$_2R^1$, —CON$R^1$(CH$_2$)CO$_2$H, —SO$_2$H, —PO$_3$H$_2$,

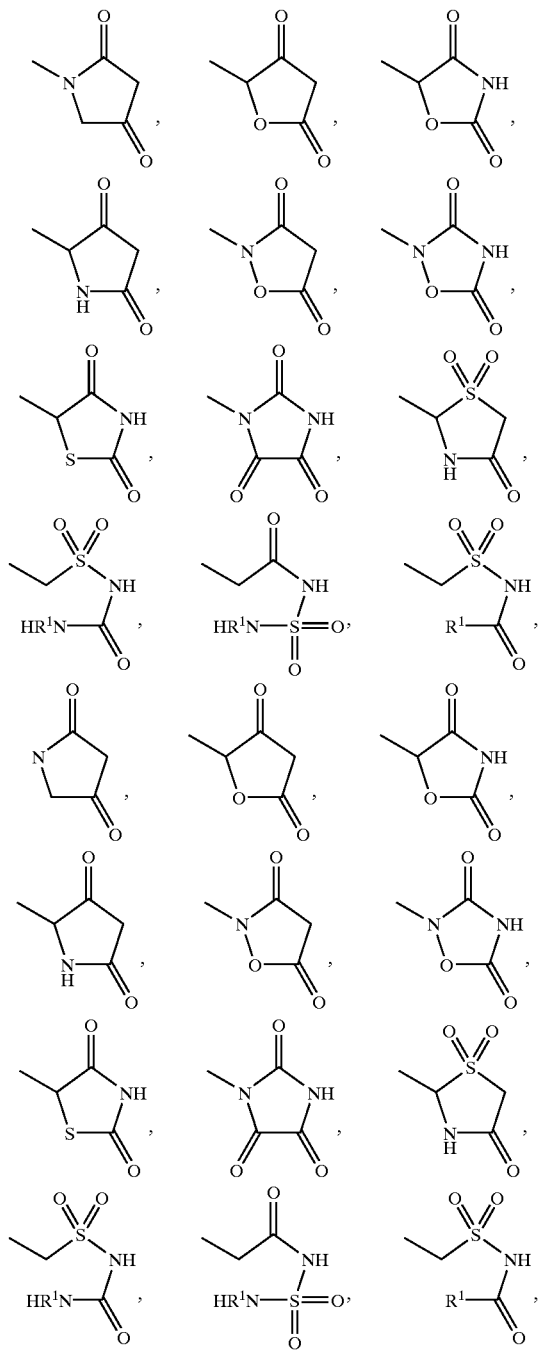

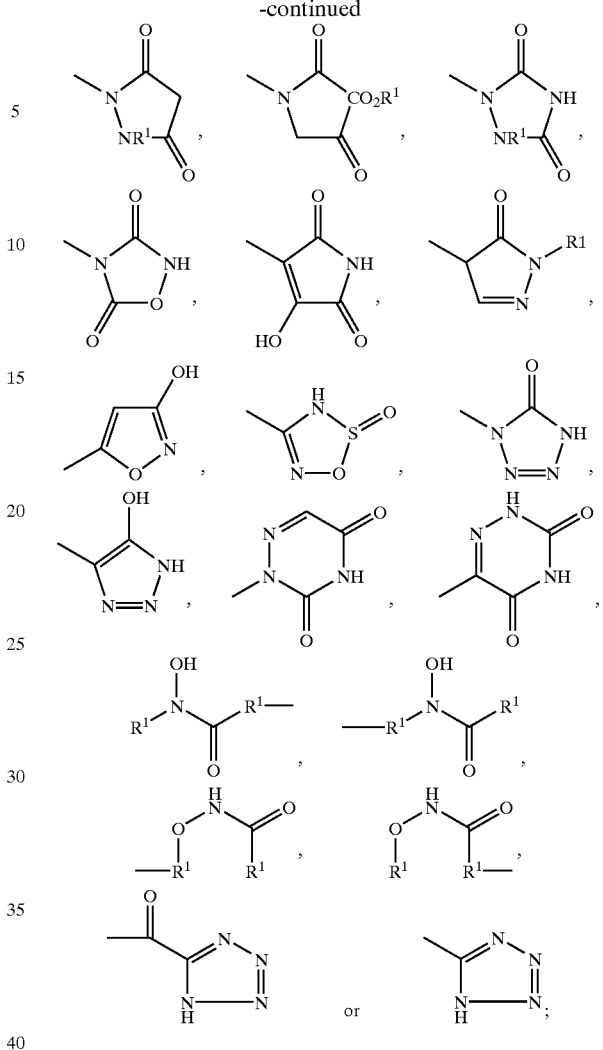

each $R^3$ is independently selected from H and $R^2$;

$R^4$ is —(CH$_2$)$_t$(C$_6$–C$_{10}$ aryl), or —(CH$_2$)$_t$(4 to 10 membered heterocyclic), wherein t is an integer from zero to five; said alkyl group optionally including one or two hetero moieties selected from O, S and —N($R^5$)— with the proviso that two O atoms, two S atoms, or an O and S atom are not attached directly to each other; said aryl and heterocyclic $R^4$ groups are optionally fused to a $C_6$–$C_{10}$ aryl group, a $C_5$–$C_8$ saturated cyclic group, or a 4 to 10 membered heterocyclic group; one or two carbon atoms of the heterocyclic moieties of $R^4$ being optionally substituted by an oxo (=O) moiety; the —(CH$_2$)$_t$— moieties of $R^4$ optionally including a carbon-carbon double or triple bond where t is an integer from two to five, $R^4$ being optionally substituted by one to five $R^5$ groups;

$R^{11}$ and $R^{10}$ are each independently $R^1$; $R^{11}$ and $R^{10}$, together with the carbons to which $R^{11}$ and $R^{10}$ are attached optionally forming a 4 to 10 membered carbocyclic group optionally substituted by =O or H(OH) or a 4 to 10 membered heterocyclic group comprising heterocyclic moieties selected from O, N or S optionally substituted with $R^1$, S, SO or SO$_2$; said carbocyclic group or heterocyclic group formed by $R^{11}$ and $R^{10}$ being optionally fused to a $C_6$–$C_{10}$ aryl group, a $C_5$–$C_8$ saturated cyclic group, or a 4 to 10 membered heterocyclic group optionally substituted with one or more substituents selected from halogen, hydroxy, $C_1$–$C_{10}$ alkyl, $C_1$–$C_{10}$ alkoxy and methylenedioxy;

Y and Z are independently CH, N optionally substituted with $R^1$, O, S, SO or $SO_2$;

m is zero or 1;

n is zero to 6;

v is zero or 1.

Preferred compounds include those of formula I wherein $R^1$ is H, $C_1$–$C_{10}$ alkyl, $C_2$–$C_{10}$ alkenyl, $C_2$–$C_{10}$ alkynyl, $C_6$–$C_{10}$ aryl, or a 4 to 10 membered heterocyclic group, wherein any aromatic carbocyclic or heterocyclic rings are optionally substituted with one or more substituents selected from halogen, hydroxy, $C_1$–$C_6$alkoxy, $C_1$–$C_6$alkyl, $CF_3$, $CO_2H$, $CO_2$alkyl or CN.

Other preferred compounds are those in which $R^2$ is —$CO_2H$, —$CONHSO_2R^1$, —$CONR^1(CH_2)CO_2H$,

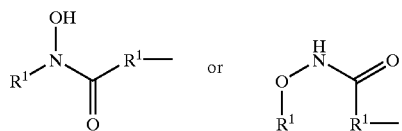

Other preferred compounds include those wherein $R_2$ is meta-substituted benzoic acid or phenylacetic acetic acid.

Other preferred compounds are those wherein $R^4$ is phenyl or a 4 to 10 membered heterocyclic group optionally substituted with one or more substituents selected from halogen, hydroxy, $C_1$–$C_6$alkoxy, $C_1$–$C_6$alkyl, or methylenedioxy.

Other preferred compounds are those wherein Y and Z are independently selected from CH and N.

Another preferred class of compounds comprises compounds of the formula (II)

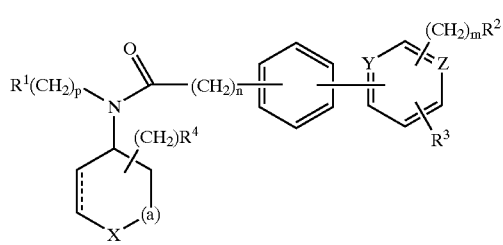

wherein $R^1$, $R^2$, $R^3$, $R^4$, m, n, p, Y and Z are as defined for formula (I), X is $CHR^1$, O, N optionally substituted with $R^1$, S, SO or $SO_2$, a is zero, 1 or 2; and the dotted line indicates optional fusion to a $C_6$–$C_{10}$ aryl group, a $C_5$–$C_8$ saturated cyclic group, or a 4 to 10 membered heterocyclic group, each optionally substituted with one or more substituents selected from halogen, hydroxy, $C_1$–$C_{10}$ alkyl, $C_1$–$C_{10}$ alkoxy and methylenedioxy.

Specific preferred compounds of the present invention include:

trans-3'-{[Benzyl-(2-benzyl-1,2,3,4-tetrahydro-naphthalen-1-yl)-carbamoyl]-methyl}-biphenyl-3-carboxylic acid;

trans-2'-{[Benzyl-(2-benzyl-1,2,3,4-tetrahydro-naphthalen-1-yl)-carbamoyl]-methyl}-biphenyl-2-carboxylic acid;

trans-2'-{[Benzyl-(2-benzyl-1,2,3,4-tetrahydro-naphthalen-1-yl)-carbamoyl]-methyl}-biphenyl-3-carboxylic acid;

trans-2'-{[Benzyl-(2-benzyl-1,2,3,4-tetrahydro-naphthalen-1-yl)-carbamoyl]-methyl}-biphenyl-4-carboxylic acid;

trans-3'-{[Benzyl-(2-benzyl-1,2,3,4-tetrahydro-naphthalen-1-yl)-carbamoyl]-methyl}-biphenyl-2-carboxylic acid;

trans-3'-{[Benzyl-(2-benzyl-1,2,3,4-tetrahydro-naphthalen-1-yl)-carbamoyl]-methyl}-biphenyl-4-carboxylic acid;

trans-4'-{[Benzyl-(2-benzyl-1,2,3,4-tetrahydro-naphthalen-1-yl)-carbamoyl]-methyl}-biphenyl-2-carboxylic acid;

trans-4'-{[Benzyl-(2-benzyl-1,2,3,4-tetrahydro-naphthalen-1-yl)-carbamoyl]-methyl}-biphenyl-3-carboxylic acid;

trans-4'-{[Benzyl-(2-benzyl-1,2,3,4-tetrahydro-naphthalen-1-yl)-carbamoyl]-methyl}-biphenyl-4-carboxylic acid;

trans-6-(3-{[Benzyl-(2-benzyl-1,2,3,4-tetrahydro-naphthalen-1-yl)-carbamoyl]-methyl}-phenyl)-pyridine-2-carboxylic acid;

trans-3'-{[(2-Benzyl-1,2,3,4-tetrahydro-naphthalen-1-yl)-furan-2-ylmethyl-carbamoyl]-methyl}-biphenyl-3-carboxylic acid;

trans-3'-{[(2-Benzyl-1,2,3,4-tetrahydro-naphthalen-1-yl)-furan-3-ylmethyl-carbamoyl]-methyl}-biphenyl-3-carboxylic acid;

trans-3'-{[(2-Benzyl-1,2,3,4-tetrahydro-naphthalen-1-yl)-isoxazol-5-ylmethyl-carbamoyl]-methyl}-biphenyl-3-carboxylic acid;

trans-3'-({Benzyl-[2-(3-methoxy-benzyl)-1,2,3,4-tetrahydro-naphthalen-1-yl]-carbamoyl}-methyl)-biphenyl-3-carboxylic acid;

trans-3'-{[Benzyl-(2-benzyl-6-methoxy-1,2,3,4-tetrahydro-naphthalen-1-yl)-carbamoyl]-methyl}-biphenyl-3-carboxylic acid;

trans-N-Benzyl-N-(2-benzyl-1,2,3,4-tetrahydro-naphthalen-1-yl)-2-[3'-(4-fluorobenzenesulfonylaminocarbonyl)-biphenyl-3-yl]-acetamide;

trans-N-Benzyl-N-(2-benzyl-1,2,3,4-tetrahydro-naphthalen-1-yl)-2-(3'-methanesulfonylaminocarbonyl-biphenyl-3-yl)-acetamide;

trans-N-Benzyl-N-(2-benzyl-1,2,3,4-tetrahydro-naphthalen-1-yl)-2-(3'-trifluoromethanesulfonylaminocarbonyl-biphenyl-3-yl)-acetamide;

trans-N-Benzyl-N-(2-benzyl-1,2,3,4-tetrahydro-naphthalen-1-yl)-2-(3'-ethanesulfonylaminocarbonyl-biphenyl-3-yl)-acetamide;

trans-N-Benzyl-N-(2-benzyl-1,2,3,4-tetrahydro-naphthalen-1-yl)-2-[3'-(3,4-difluorobenzenesulfonylaminocarbonyl)-biphenyl-3-yl]-acetamide;

trans-2-[(3'-{[Benzyl-(2-benzyl-1,2,3,4-tetrahydro-naphthalen-1-yl)-carbamoyl]-methyl}-biphenyl-3-carbonyl)-sulfamoyl]-benzoic acid methyl ester;

trans-2-[(3'-{[Benzyl-(2-benzyl-1,2,3,4-tetrahydro-naphthalen-1-yl)-carbamoyl]-methyl}-biphenyl-3-carbonyl)-sulfamoyl]-benzoic acid;

trans-[(3'-{[Benzyl-(2-benzyl-1,2,3,4-tetrahydro-naphthalen-1-yl)-carbamoyl]-methyl}-biphenyl-3-carbonyl)-amino]-acetic acid;

trans-3'-{[Benzyl-(2-benzyl-cyclohexyl)-carbamoyl]-methyl}-biphenyl-3-carboxylic acid;

cis-3'-{[Benzyl-(2-benzyl-cyclohexyl)-carbamoyl]-methyl}-biphenyl-3-carboxylic acid;

cis-2-[(3'-{[Benzyl-(2-benzyl-cyclohexyl)-carbamoyl]-methyl}-biphenyl-3-carbonyl)-sulfamoyl]-benzoic acid methyl ester;

cis-2-[(3'-{[Benzyl-(2-benzyl-cyclohexyl)-carbamoyl]-methyl}-biphenyl-3-carbonyl)-sulfamoyl]-benzoic acid;

cis-3'-{[(2-Benzyl-1,2,3,4-tetrahydro-naphthalen-1-yl)-isopropyl-carbamoyl]-methyl}-biphenyl-3-carboxylic acid;

trans-3'-{[(2-Benzyl-1,2,3,4-tetrahydro-naphthalen-1-yl)-isopropyl-carbamoyl]-methyl}-biphenyl-3-carboxylic acid;

3'-{[(2-Benzyl-cyclohexyl)-methyl-carbamoyl]-methyl}-biphenyl-3-carboxylic acid;

trans-3'-{[(2-Benzyl-1,2,3,4-tetrahydro-naphthalen-1-yl)-(4-carboxy-benzyl)-carbamoyl]-methyl}-biphenyl-3-carboxylic acid;

trans-3'-{[(2-Benzyl-1,2,3,4-tetrahydro-naphthalen-1-yl)-(3-carboxy-benzyl)-carbamoyl]-methyl}-biphenyl-3-carboxylic acid;

The invention also relates to a pharmaceutical composition for the treatment of a hyperproliferative disorder in a mammal which comprises a therapeutically effective amount of a compound of formula I, or a pharmaceutically acceptable salt or hydrate thereof, and a pharmaceutically acceptable carrier. In one embodiment, said pharmaceutical composition is for the treatment of cancer such as brain, lung, squamous cell, bladder, gastric, pancreatic, breast, head, neck, renal, prostate, colorectal, oesophageal, gynecological (such as ovarian) or thyroid cancer. In another embodiment, said pharmaceutical composition is for the treatment of a non-cancerous hyperproliferative disorder such as benign hyperplasia of the skin (e.g., psoriasis) or prostate (e.g., benign prostatic hypertropy (BPH)).

The invention also relates to a pharmaceutical composition for the treatment of pancreatitis or kidney disease (including proliferative glomerulonephritis and diabetes-induced renal disease) in a mammal which comprises a therapeutically effective amount of a compound of formula I, or a pharmaceutically acceptable salt or hydrate thereof, and a pharmaceutically acceptable carrier.

The invention also relates to a pharmaceutical composition for the prevention of blastocyte implantation in a mammal which comprises a therapeutically effective amount of a compound of formula I, or a pharmaceutically acceptable salt or hydrate thereof, and a pharmaceutically acceptable carrier.

The invention also relates to a pharmaceutical composition for treating a disease related to vasculogenesis or angiogenesis in a mammal which comprises a therapeutically effective amount of a compound of formula I, or a pharmaceutically acceptable salt or hydrate thereof, and a pharmaceutically acceptable carrier. In one embodiment, said pharmaceutical composition is for treating a disease selected from the group consisting of tumor angiogenesis, chronic inflammatory disease such as rheumatoid arthritis, atherosclerosis, skin diseases such as psoriasis, excema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a method of treating a hyperproliferative disorder in a mammal which comprises administering to said mammal a therapeutically effective amount of the compound of formula I or a pharmaceutically acceptable salt or hydrate thereof. In one embodiment, said method relates to the treatment of cancer such as brain, squamous cell, bladder, gastric, pancreatic, breast, head, neck, oesophageal, prostate, colorectal, lung, renal, gynecological (such as ovarian) or thyroid cancer. In another embodiment, said method relates to the treatment of a non-cancerous hyperproliferative disorder such as benign hyperplasia of the skin (e.g., psoriasis) or prostate (e.g., benign prostatic hypertropy (BPH)).

The invention also relates to a method for the treatment of a hyperproliferative disorder in a mammal which comprises administering to said mammal a therapeutically effective amount of a compound of formula I or a pharmaceutically acceptable salt or hydrate thereof, in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

The invention also relates to a method of treating pancreatitis or kidney disease in a mammal which comprises administering to said mammal a therapeutically effective amount of a compound of formula I or a pharmaceutically acceptable salt or hydrate thereof.

The invention also relates to a method of preventing blastocyte implantation in a mammal which comprises administering to said mammal a therapeutically effective amount of a compound of formula I or a pharmaceutically acceptable salt or hydrate thereof.

The invention also relates to a method of treating diseases related to vasculogenesis or angiogenesis in a mammal which comprises administering to said mammal an effective amount of a compound of formula I or a pharmaceutically acceptable salt or hydrate thereof. In one embodiment, said method is for treating a disease selected from the group consisting of tumor angiogenesis, chronic inflammatory disease such as rheumatoid arthritis, atherosclerosis, skin diseases such as psoriasis, excema, and scleroderma, diabetes, diabetic retinopathy, retinopathy of prematurity, macular degeneration, hemangioma, glioma, melanoma, Kaposi's sarcoma and ovarian, breast, lung, pancreatic, prostate, colon and epidermoid cancer.

Further, the compounds of the present invention may be used as contraceptives in mammals.

Patients that can be treated with the compounds of formula I and the pharmaceutically acceptable salts and hydrates of said compounds according to the methods of this invention include, for example, patients that have been diagnosed as having psoriasis, BPH, lung cancer, bone cancer, pancreatic cancer, skin cancer, cancer of the head and neck, cutaneous or intraocular melanoma, uterine cancer, ovarian cancer, rectal cancer or cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphonas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

The invention is further directed to a process for forming a compound of formula I

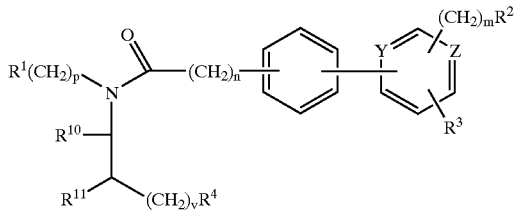

which comprises reacting a compound of formula V

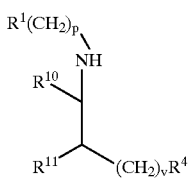

with a compound of formula IX

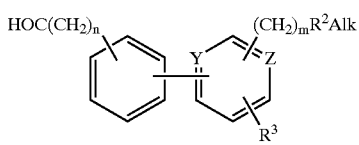

to form a precursor of formula X

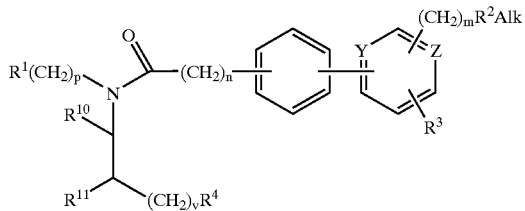

and hydrolyzing the precursor of formula X in a strong base, wherein $R^1, R^2, R^3, R^4, R^{10}, R^{11}$, m, n, p and v are as defined for formula I and Alk is alkyl.

The term "halo", as used herein, unless otherwise indicated, includes fluoro, chloro, bromo or iodo. Preferred halo groups are fluoro, chloro and bromo.

The term "alkyl", as used herein, unless otherwise indicated, includes saturated monovalent hydrocarbon radicals having straight, cyclic or branched moieties. It is understood that for cyclic moieties at least three carbon atoms are required in said alkyl group.

The term "alkenyl", as used herein, unless otherwise indicated, includes monovalent hydrocarbon radicals having at least one carbon-carbon double bond and also having straight, cyclic or branched moieties as provided above in the definition of "alkyl".

The term "alkynyl", as used herein, unless otherwise indicated, includes monovalent hydrocarbon radicals having at least one carbon-carbon triple bond and also having straight, cyclic or branched moieties as provided above in the definition of "alkyl".

The term "alkoxy", as used herein, unless otherwise indicated, includes O-alkyl groups wherein "alkyl" is as defined above.

The term "aryl", as used herein, unless otherwise indicated, includes an organic radical derived from an aromatic hydrocarbon by removal of one hydrogen, such as phenyl or naphthyl.

The term "4 to 10 membered heterocyclic", as used herein, unless otherwise indicated, includes aromatic and non-aromatic heterocyclic groups containing one or more heteroatoms each selected from O, S and N, wherein each heterocyclic group has from 4 to 10 atoms in its ring system. Non-aromatic heterocyclic groups include groups having only 4 atoms in their ring system, but aromatic heterocyclic groups must have at least 5 atoms in their ring system. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

The phrase "pharmaceutically acceptable salt(s)", as used herein, unless otherwise indicated, includes salts of acidic or basic groups which may be present in the compounds of formula I. The compounds of formula I that are basic in nature are capable of forming a wide variety of salts with various inorganic and organic acids. The acids that may be used to prepare pharmaceutically acceptable acid addition salts of such basic compounds of formula I are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Those compounds of the formula I that are acidic in nature are capable of forming base salts with various pharmacologically acceptable cations. Examples of such salts include the alkali metal or alkaline earth metal salts and particularly, the sodium and potassium salts.

Certain compounds of formula I may have asymmetric centers and therefore exist in different enantiomeric forms. This invention relates to the use of all optical isomers and stereoisomers of the compounds of formula I and mixtures thereof. The compounds of formula I may also exist as tautomers. This invention relates to the use of all such tautomers and mixtures thereof.

The subject invention also includes isotopically-labelled compounds, and the pharmaceutically acceptable salts thereof, which are identical to those recited in formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2H$, $^3H$, $^{13}C$, $^{14}C$, $^{15}N$, $^{18}O$, $^{17}O$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of formula I of this invention and prodrugs thereof can generally be prepared by carrying out the procedures disclosed in the Schemes and/or in the Examples and Preparations below, by substituting a readily available isotopically labelled reagent for a non-isotopically labeled reagent.

This invention also encompasses pharmaceutical compositions containing, and methods of treating diseases related to vasculogenesis or angiogenesis in mammals through administration of prodrugs of, compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula I. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs are also encompassed. For instance, free carboxyl groups can be derivatized as amides or alkyl esters. The amide and ester moieties may incorporate groups including but not limited to ether, amine and carboxylic acid functionalities. Free hydroxy groups may be derivatized using groups including but not limited to hemisuccinates, phosphate esters, dimethylaminoacetates, and phosphoryloxymethyloxycarbonyls, as outlined in D. Fleisher, R. Bong, B. H. Stewart, Advanced Drug Delivery Reviews (1996) 19, 115. Carbamate prodrugs of hydroxy and amino groups are also included, as are carbonate prodrugs and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in R. P. Robinson et al., J. Medicinal Chemistry (1996) 39, 10.

DETAILED DESCRIPTION OF THE INVENTION

Compounds of the formula I and their pharmaceutically acceptable salts and hydrates may be prepared as described below. Unless otherwise indicated, $R^1$, $R^2$, $R^3$, $R^4$, $R^{10}$, $R^{11}$, m, n, p and v are as defined above, Alk is alkyl and Hal is halogen.

Scheme 1

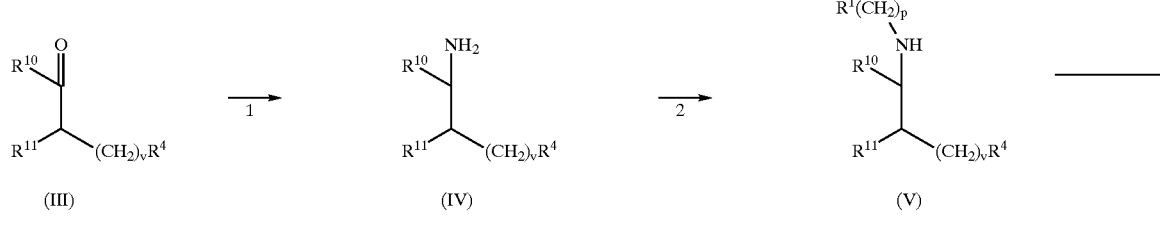

-continued
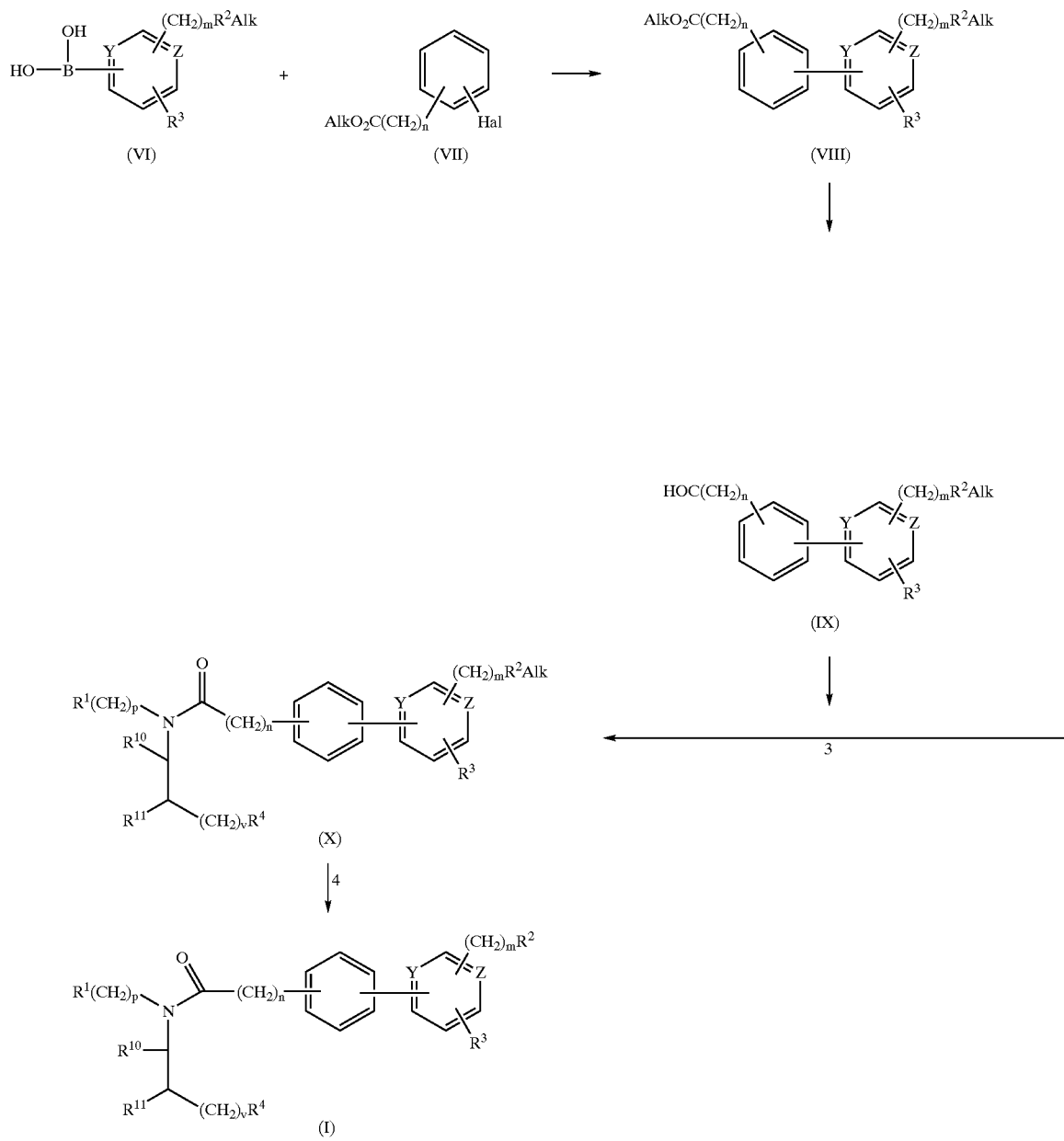
Scheme 2
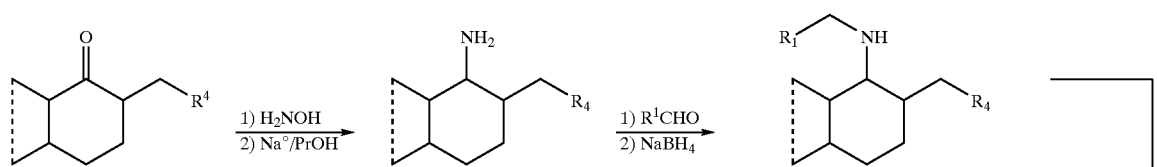

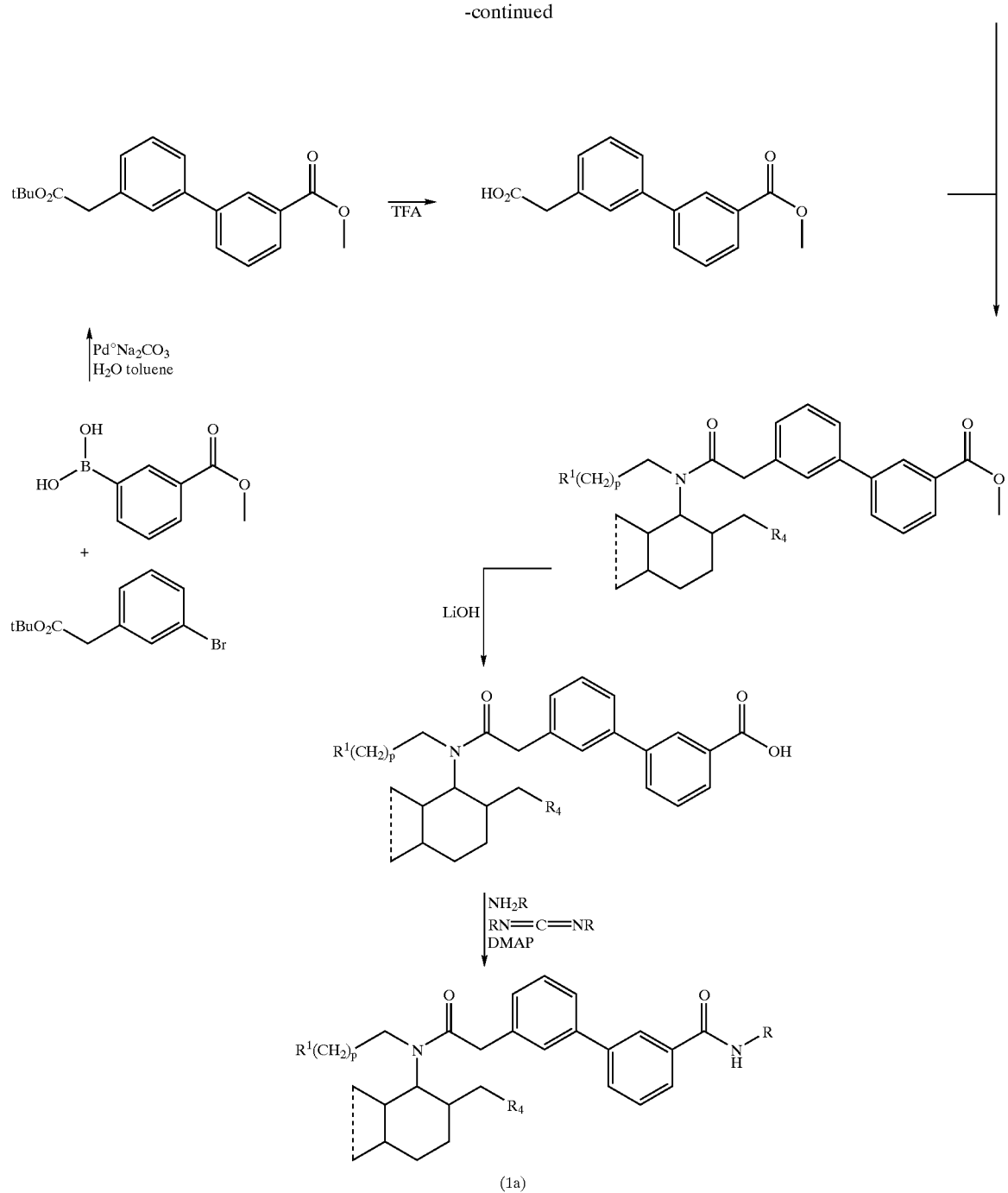

(1a)

The compounds of the present invention are readily prepared by following the procedures outlined in the schemes illustrated above and typical synthetic procedures familiar to those skilled in the art. Schemes 1 and 3 show the conversion of a ketone to oxime and reduction to a primary amine, conversion of the primary amine to a secondary amine. The secondary amine is reacted with a biaryl carboxylic acid that is formed by condensing a phenyl acetic acid ester and an aryl bromide. The reaction of said secondary amine and biaryl carboxylic acid yields a biaryl acetamide alkyl carboxylate that can be subjected to base hydrolysis to provide a biaryl acetamide carboxylic acid. In step 1 of Scheme 1, the compound of formula IV may be prepared by treating the compound of formula III with $H_2NOH$ in a suitably strong base, such as an alkali metal salt of a carboxylic acid, preferably sodium acetate, or an amine base (e.g., ammonia) in a protic solvent, such as an alcohol, preferably ethanol, at a temperature ranging from about 0° C. to about 150° C., preferably between about 20° C. and about 80° C. for a period of about 1 hours to about 48 hours. In step 2 of Scheme 1, the compound of formula IV may be reacted at a temperature ranging from about 0° C. to about 150° C., preferably between about 80° C. and about 110° C. for a period of about 0.5 hours to about 24 hours with an aldehyde (RCHO) to form an intermediate imine, which in turn is reduced to a secondary amine (of formula V) using a hydride source, such as sodium borohydride. In step 3 of Scheme 1, the compound of formula V is reacted with a compound of formula IX at a temperature ranging from about −20° C. to about 150° C., preferably between about 0° C. and about 180° C. for a period of about 0.5 hours to about 48 hours to form a compound of formula X. The compound of formula IX may be formed by condensing a phenyl acetic acid ester of formula VI and an aryl halide of formula VII at a temperature ranging from about 20° C. to about 150° C., preferably between about 50° C. and about 110° C. for a period of about 0.5 hours to about 24 hours (a Suzuki reaction) to form a compound of formula VIII, from which the alkyl group (e.g., t-butyl group) is cleaved (using for example trifluoroacetic acid) to provide the biaryl carboxylic acid ester of formula IX. The compound of formula X can be base hydrolyzed to provide the compound of formula I. Scheme 2 shows a more specific reaction for forming a compound of formula I (in the form of a preferred compound of formula II). In scheme 2, the various reactants are numbered to correspond with those of Scheme 1. Scheme 2 further shows an optional derivitization of the compound of formula I with an amine to provide a compound of formula Ia.

The compounds of the present invention may have asymmetric carbon atoms. Such diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomer mixtures and pure enantiomers are considered as part of the invention.

The compounds of formula I that are basic in nature are capable of forming a wide variety of different salts with various inorganic and organic acids. Although such salts must be pharmaceutically acceptable for administration to animals, it is often desirable in practice to initially isolate the compound of formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of formula I that are acidic in nature, are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of formulas I. Such non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

Included in the present invention are compounds identical to the compounds of formula I but for the fact that one or more hydrogen or carbon atoms are replaced by isotopes thereof. Such compounds are useful as research and diagnostic tools in metabolism pharmokinetic studies and in binding assays. Specific applications in research include radioligand binding assays, autoradiography studies and in vivo binding studies. Included among the radiolabeled forms of the compounds of formula I are the tritium and $C^{14}$ isotopes thereof.

The in vitro activity of the compounds of formula I in inhibiting VEGF/GAG (glycosaminoglycan) binding may be measured using the assay described in U.S. Pat. No. 5,795,860, the subject matter of which is incorporated herein by reference.

Using mixed cellulose ester 96-well filter plates, 150 $\mu$L of Dulbeccos PBS (phosphate buffered saline) containing 10% ovalbumin is added. Compound (5.0 $\mu$L) is added at a final concentration of 1.8 $\mu$M. Compounds are dissolved in 8% DMSO (final DMSO concentration is 0.16%) and tested at concentrations of 32, 10, 3.2, 1.0, 0.32 and 0.10 $\mu$M. A mixture of $[^{125}I]$heparin-16-mer (4500 cpm per well), purified $VEGF_{165}$ (20 nM final concentration/well, prepared by Repligen, Inc.) and Dulbeccos PBS with 10% ovalbumin is added to the 96-well plate in a volume of 100 $\mu$L. Nonspecific binding is defined using 10 $\mu$M heparin-sodium from porcine intestinal mucosa. The assay plate is incubated for 60 minutes at room temperature, filtered using a Millipore filtration apparatus, the plastic bottom plate is removed and the filter plate is allowed to completely dry. The plate bottom is sealed with plastic plate seal and 25 $\mu$L of scintillation cocktail is added to each well. The top plate is sealed and is counted for radioactivity on a Microbeta Scintillation Counter. The assay is run in a final volume of 250 $\mu$L.

The activity of the compounds of formula I, in vivo, can be determined by the amount of inhibition of tumor growth by a test compound relative to a control. The tumor growth inhibitory effects of various compounds are measured according to the methods of Corbett T. H., et al. "Tumor Induction Relationships in Development of Transplantable Cancers of the Colon in Mice for Chemotherapy Assays, with a Note on Carcinogen Structure", Cancer Res., 35, 2434–2439 (1975) and Corbett, T. H., et al., "A Mouse Colon-tumor Model for Experimental Therapy", Cancer Chemother. Rep. (Part 2)", 5, 169–186 (1975), with slight modifications. Tumors are induced in the flank by s.c. injection of $1\times10^6$ log phase cultured tumor cells suspended in 0.1–0.2 ml PBS. After sufficient time has elapsed for the tumors to become palpable (5–6 mm in diameter), the test animals (athymic mice) are treated with active compound (formulated by dissolution in appropriate diluent, for example water or 5% Gelucire™ 44/14 rn PBS by the intraperitoneal (ip) or oral (po) routes of administration once or twice daily for 4 to 10 consecutive days. In order to determine an anti-tumor effect, the tumor is measured in millimeters with Vernier calipers across two diameters and the tumor volume (mm$^3$) is calculated using the formula: Tumor weight=(length×[width]$^2$)/2, according to the methods of Geran, R. I., et al. "Protocols for Screening Chemical Agents and Natural Products Against Animal Tumors and Other Biological Systems", Third Edition, *Cancer Chemother. Rep.*, 3, 1–104 (1972). The flank site of tumor implantation provides reproducible dose/response effects for a variety of chemotherapeutic agents, and the method of measurement (tumor diameter) is a reliable method for assessing tumor growth rates.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The amount of the active compound administered will be dependent on the subject being treated, the severity of the disorder or condition, the rate of administration and the judgement of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or may involve one or more other anti-tumour substances, for example those selected from, for example, mitotic inhibitors, for example vinblastine; alkylating agents, for example cis-platin, carboplatin and cyclophosphamide; anti-metabolites, for example 5-fluorouracil, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences*, Mack Publishing Company, Easter, Pa., 15th Edition (1975).

The examples and preparations provided below further illustrate and exemplify the compounds of the present invention and methods of preparing such compounds. It is to be understood that the scope of the present invention is not limited in any way by the scope of the following examples and preparations.

Preparation A

2-Benzyl-3,4-dihydro-2H-naphthalen-1-one oxime:

To a solution of 2-benzyl-1-tetralone (prepared according to Org. Prep. Proc. Inter., 2, 37 (1970)), (58.95 g, 0.250 mol) and 95% ethanol (500 mL) was added sodium acetate (45.1 g, 0.55 mol) and hydroxylamine hydrochloride (20.8 g, 0.30 mol). The reaction was heated to reflux overnight and then allowed to cool to room temperature and concentrated under vacuum. The residue was partitioned between water (300 mL) and ethryl acetate (500 mL), the organic layer was then sequentially washed with water (300 mL), and brine (500 mL). This was then dried over sodium sulfate and concentrated to give 61.1 g of an orange solid. Recrystalization from ethyl acetate/hexanes gave the title compound as a white solid, m.p. 123–124° C.

$^1$H-NMR (CDCl$_3$, δ): 1.8 (m, 2H), 2.61 (dd, J=11.4, 13.5 Hz, 1H), 2.69 (m, 1H), 3.03 (ddd, J=6.0, 11, 17 Hz, 1H), 3.16 (dd, J=4.1, 13 Hz, 1H), 3.87 (ddd, J=4.0, 4.0, 11 Hz, 1H), 7.1–7.3 (m, 8 H), 7.95 (d, J=7.7 Hz, 1H), 8.82 (br s, 1H).

$^{13}$C-NMR (CDCl$_3$, δ): 23.6, 25.0, 33.8, 34.5, 124.5, 126.2, 126.5, 128.4, 129.0, 129.2, 129.3, 129.9, 138.7, 140.1, 158.1.

MS, APCI (%): 252 (M+1, 100), 234 (25)

Preparation B

1-Amino-2-benzyltetralin:

To a solution of the oxime from preparation A (15.0 g, 59.7 mmol) and dry isopropanol (1 L) which had been heated to reflux was added sodium metal spheres (74 g, 3.2 mol) over 1 h. The reaction mixture was heated to reflux for an additional 4 h, and then allowed to stand at room temperature overnight. Water (500 mL) was cautiously added to the now solid reaction mixture, and concentrated HCl was added until pH 1. The mixture was concentrated to a solid and then partitioned between water (500 mL) and ether (1 L). The remaining aqueous solution was made basic with solid NaOH and then extracted with ether (3×500 mL). These latter combined organic layers were washed with brine (500 mL), dried ($K_2CO_3$) and concentrated to give 10.5 g of the title compound (1:1 mixture of cis/trans isomers) as a pale yellow oil.

$^1$H-NMR (CDCl$_3$, δ): 1.4–2.2 (m, 3H), 2.49 (dd, J=8.9, 14 Hz, 1H), 2.6–2.9 (m), 2.96 (dd, J=5.5, 14 Hz, 1H), 3.70 (d, J=5.6 Hz, 1H), 3.81 (d, J=3.5 Hz, 1H).

MS, APCI (%): 237 (M+1, 6), 221 (100).

Preparation C

1-Benzylamino-2-benzyltetralin:

To a solution of the product of preparation B (10.5 g, 44.4 mmol) and toluene (200 mL) was added benzaldehyde (4.74 mL, 46.6 mmol) and p-toluenesulfonic acid (1.0 g, 5.3 mmol). The reaction was heated to reflux for 18 h and the water produced was collected in a Dean-Stark trap. After cooling, the reaction was partitioned between NaHCO$_3$ (2% aqueous, 200 mL) and ethyl acetate (500 mL), dried (Na$_2$SO$_4$) and concentrated to afford an intermediate imine which was dilute immediately with dry methanol (400 mL). Reduction was effected by the portionwise addition of NaBH4 (10.0 g, 0.264 mol) and stirring was continued for 3 h at room temperature. The reaction mixture was concentrated to dryness and partitioned between water (300 mL) and ethyl acetate (500 mL). The organic layer was dried (Na$_2$SO$_4$) and concentrated to afford a cis/trans isomeric mixture of the title compound. Chromatography of this product on silica gel with ethyl acetate/hexanes mixture afforded the separate isomers:

Less polar diastereomer, assigned cis stereochemistry based on an X-ray crystal, 5.00 g (34%), as an oil.

$^1$H-NMR (CDCl$_3$, δ): 1.7–1.9 (m, 2H), 2.2 (m, 1H), 2.75 (m, 2H), 2.94 (ddd, J=3.5, 6.5, 17 Hz, 1H), 3.03 (dd, J=7.0, 13 Hz, 1H), 3.61 (d, J=3.5 Hz, 1H), 3.83 (d, J=12.9 Hz, 1H), 3.96 (d, J=12.9 Hz, 1H), 7.1–7.5 (m, 14H).

MS, APCI (%): 328 (M+1, 40), 221 (100).

More polar trans diastereomer, 5.27 g (36%), as an oil.

$^1$H-NMR (CDCl$_3$, δ): 1.6 (m, 2H), 2.10 (m, 1H), 2.3 (m, 1H), 2.49 (dd, J=8.3, 13 Hz, 1H), 2.8 (m, 2H), 3.58 (d, J=4.3 Hz, 1H), 3.68 (d, J=13.2 Hz, 1H), 3.74 (d, J=13.2 Hz, 1H), 7.0–7.4 (m, 14H).

MS, APCI (%): 328 (M+1, 30), 221 (100).

Also prepared by a similar method was:

trans-(2-Benzyl-1,2,3,4-tetrahydro-naphthalen-1-yl)-furan-2-ylmethyl-amine:

$^1$H-NMR (CDCl$_3$, δ): 1.6 (m, 1H), 2.1 (m, 1H), 2.3 (m, 1H), 2.48 (dd, J=8.0, 13 Hz, 1H), 2.65 (dd, J=7.2, 13 Hz, 1H), 2.8 (m, 2H), 3.53 (d, J=3.7 Hz), 3.68 (d, J=15 Hz, 1H), 3.75 (d, J=15 Hz, 1H), 5.97 (dd, J=2.7, 3.1 Hz, 1H), 6.27 (dd, J=1.9, 3.1 Hz, 1H), 7.1–7.4 (m, 10H).

MS (FAB, %): 318 (M+1, 30), 221 (40), 129 (40).

trans-(2-Benzyl-1,2,3,4-tetrahydro-naphthalen-1-yl)-furan-3-ylmethyl-amine:

$^1$H-NMR (CDCl$_3$, δ): 1.6 (m, 1H), 2.1 (m, 1H), 2.3 (m, 1H), 2.54 (dd, J=8.0, 13 Hz, 1H), 2.68 (dd, J=8.0, 13 Hz, 1H), 2.8 (m, 2H), 3.60 (app d, J=3.7 Hz, 3H) 6.36 (s, 1H), 7.1–7.4 (m, 12H).

MS (FAB, %): 318 (M+1, 100), 221 (60).

Preparation D (3-Bromo-phenyl)-acetic acid tert-butyl ester:

To a solution of 3-bromo-phenyl-acetic acid (10 gm, 46.5 mmol) and methylene chloride (47 mL) was added a solution of t-butyl-2,2,2-trichloroacetamidate (20.3 g, 93.0 mmol) and cyclohexane (186 mL) followed by borontrifluoride etherate (0.93 mL, 7.3 mmol). After stirring overnight, solid sodium bicarbonate was added and the reaction then filtered through a pad of silica gel utilizing methylene chloride as solvent. Concentration gave 9.11 g (72%) of a colorless oil.

$^1$H-NMR (CDCl$_3$, δ): 1.41 (s, 9H), 3.46 (s, 2H), 7.1–7.4 (multiplets, 4H).

Also prepared by this method were:

(2-Bromo-phenyl)-acetic acid tert-butyl ester:

$^1$H-NMR (CDCl$_3$, δ): 1.45 (s, 9H), 3.69 (s, 2H), 7.11 (m, 1H), 7.25 (m, 1H), 7.55 (d, J=7.9 Hz, 1H).

(4-Bromo-phenyl)-acetic acid tert-butyl ester:

$^1$H-NMR (CDCl$_3$, δ): 1.42 (s, 9H), 3.46 (s, 2H), 7.13 (d, J=8.3 Hz, 1H), 7.42 (d, J=8.3 Hz, 1H).

Preparation E

3'-tert-Butoxycarbonylmethyl-biphenyl-3-carboxylic acid methyl ester:

To a solution of the product of preparation D (9.11 g, 33.6 mmol), 3-carbomethoxy phenylboronic acid (6.11 g, 33.6 mmol), toluene (91 mL), isopropanol (45 mL) and water (45 mL) was added sodium carbonate (7.12 g, 67.2 mmol). The reaction mixture was evacuated and refilled with nitrogen three time and tetrakis(triphenylphosphine)palladium (1.16 g, 1.00 mmol) was added and the degassing was repeated. After heating to reflux for 1.5 h, the reaction was cooled, poured into water (250 mL) and extracted with ethyl acetate (3×200 mL). The combined organic layers were washed with brine (200 mL), dried (sodium sulfate), and concentrated. The title compound was isolated in 63% yield as an oil following chromatography on silica gel utilizing ethyl acetate/hexane as solvent.

$^1$H-NMR (CDCl$_3$, δ): 1.43 (s, 9H), 3.56 (s, 2H), 3.92 (s, 3H), 7.15 (d, 1H), 7.39 (t, 1H), 7.48 (m, 3H), 7.75 (d, 1H), 7.99 (d, 1H), 8.16 (s, 1H).

Also prepared by this method were:

2'-tert-Butoxycarbonylmethyl-biphenyl-3-carboxylic acid methyl ester:

$^1$H-NMR (CDCl$_3$, δ): 1.36 (s, 9H), 3.46 (s, 2H), 3.90 (s, 3H), 7.26 (m, 1H), 7.34 (m, 3H), 7.45 (dt, J=1.0, 7.7 Hz, 1H), 7.53 (dd, J=1.0, 7.7 Hz, 1H), 7.99 (t, J=1.0, Hz, 1H), 8.03 (d, J=7.7 Hz, 1H).

2'-tert-Butoxycarbonylmethyl-biphenyl-4-carboxylic acid methyl ester:

$^1$H-NMR (CDCl$_3$, δ): 1.36 (s, 9H), 3.46 (s, 2H), 3.93 (s, 3H), 7.26 (m, 1H), 7.34 (m, 3H), 7.39 (d, J=8.2 Hz, 2H), 8.07 (d, J=8.2 Hz, 2H).

3'-Benzyloxycarbonylmethyl-biphenyl-4-carboxylic acid methyl ester:

$^1$H-NMR (CDCl$_3$, δ): 3.72 (s, 2H), 3.92 (s, 3H), 5.13 (s, 2H), 7.30 (m, 6H), 7.40 (t, J=7.9 Hz, 1H), 7.51 (m, 2H), 7.59 (d, J=7.9 Hz, 2H), 8.06 (d, J=7.9 Hz, 2H).

4'-tert-Butoxycarbonylmethyl-biphenyl-3-carboxylic acid methyl ester:

¹H-NMR (CDCl₃, δ): 1.43 (s, 9H), 3.55 (s, 2H), 3.91 (s, 3H), 7.34 (d, J=8.1 Hz, 2H), 7.47 (t, J=7.8 Hz, 1H), 7.55 (d, J=8.1 Hz, 2H), 7.75 (d, J=7.7 Hz, 1H), 7.98 (d, J=7.7 Hz, 1H) 8.24 (t, J=1.8 Hz, 1H).

4'-tert-Butoxycarbonylmethyl-biphenyl-4-carboxylic acid methyl ester:

¹H-NMR (CDCl₃, δ): 1.44 (s, 9H), 3.56 (s, 2H), 3.92 (s, 3H), 7.35 (d, J=8.4 Hz, 2H), 7.57 (d, J=8.4 Hz, 2H), 7.63 (d, J=8.7 Hz, 2H), 8.08 (d, J=8.7 Hz, 2H.

Preparation F

3'-Carboxymethyl-biphenyl-3-carboxylic acid methyl ester:

To a solution of the product of preparation E (6.16 g, 18.9 mmol) and methylene chloride (90 mL) was added trifluoroacetic acid (23 mL). After stirring for 2 h, the solution was concentrated and then toluene (3×10 mL) was added and then removed under vacuum to give a white solid. The title compound was isolated as white plates (80% yield, mp 84.5–85.5° C.) following recrystallization from ethyl acetate/hexane.

¹H-NMR (CDCl₃, δ): 3.71 (s, 2H), 3.92 (s, 3H), 7.1–7.5 (multiplets, 5H), 7.75 (d, J=7.3 Hz, 1H), 7.99 (d, J=7.3 Hz, 1H), 8.24 (s, 1H).

MS, APCI (%): 269 (M−1, 100), 225 (75).

Also prepared by this method were:

2'-Carboxymethyl-biphenyl-2-carboxylic acid methyl ester:

¹H-NMR (CDCl₃, δ): 3.48 (s, 2H), 3.63 (s, 3H), 7.09 (dd, J=1.1, 7.3 Hz, 1H), 7.2–7.4 (multiplets, 5H), 7.45 (dt, J=1.2, 7.7 Hz, 1H), 7.53 (dt, J=1.5, 7.5 Hz, 1H).

2'-Carboxymethyl-biphenyl-3-carboxylic acid methyl ester:

¹H-NMR (CDCl₃, δ): 3.59 (s, 2H), 3.89 (s, 3H), 7.2–7.5 (multiplets, 6H), 7.99 (t, J=0.8 Hz, 1H), 7.53 (dt, J=0.8, 7.3 Hz, 1H).

MS, APCI (%): 269 (M−1, 10), 225 (100).

2'-Carboxymethyl-biphenyl-4-carboxylic acid methyl ester:

¹H-NMR (CDCl₃, δ): 3.60 (s, 2H), 3.93 (s, 3H), 7.2–7.4 (multiplets, 5H), 7.39 (dd, J=1.2, 7.7 Hz, 1H), 7.50 (dt, J=1.5, 7.7 Hz, 1H), 7.79 (dd, J=1.1, 7.8 Hz, 1H).

MS, APCI (%): 269 (M−1, 10), 225 (100).

3'-Carboxymethyl-biphenyl-2-carboxylic acid methyl ester:

¹H-NMR (CDCl₃, δ): 3.59 (s, 3H), 3.66 (s, 2H), 7.2–7.35 (multiplets, 5H), 8.08 (d, J=8.1 Hz, 1H).

MS, APCI (%): 269 (M−1, 75), 225 (100).

4'-Carboxymethyl-biphenyl-2-carboxylic acid methyl ester:

¹H-NMR (CDCl₃, δ): 3.64 (s, 3H), 3.70 (s, 2H), 7.2–7.35 (multiplets, 5H), 7.40 (dt, J=1.2, 7.5 Hz, 1H), 7.51 (dt, J=1.5, 7.5 Hz, 1H), 7.82 (dd, J=1.4, 7.8 Hz, 1H).

MS, APCI (%): 269 (M−1, 50), 225 (100).

4'-Carboxymethyl-biphenyl-3-carboxylic acid methyl ester:

¹H-NMR (CDCl₃, δ): 3.71 (s, 2H), 3.93 (s, 3H), 7.38 (d, J=8.2 Hz, 2H), 7.50 (t, J=7.8 Hz, 1H), 7.59 (d, J=8.2 Hz, 2H), 7.76 (dt, J=1.3, 7.7 Hz, 1H), 8.00 (dt, J=1.2, 7.7 Hz, 1H), 8.25 (t, J=1.7 Hz, 1H).

4'-Carboxymethyl-biphenyl-4-carboxylic acid methyl ester:

¹H-NMR (CDCl₃, δ): 3.71 (s, 2H), 3.93 (s, 3H), 7.38 (d, J=8.3 Hz, 2H), 7.59 (d, J=8.3 Hz, 2H), 7.63 (d, J=8.7 Hz, 2H), 8.09 (d, J=8.7 Hz, 2H).

6-(3-Carboxymethyl-phenyl)-pyridine-2-carboxylic acid methyl ester:

¹H-NMR (CDCl₃, δ): 3.74 (s, 2H), 4.01 (s, 3H), 7.35 (dt, J=1.4, 7.5 Hz, 1H), 7.44 (t, J=7.7 Hz, 1H), 7.9 (m, 3H), 7.96 (t, J=1.4 Hz, 1H), 8.06 (dd, J=3.0, 5.7 Hz, 1H).

MS, APCI (%): 270 (M−1, 40), 226 (100).

Preparation G trans-3'-{[Benzyl-(2-benzyl-1,2,3,4-tetrahydro-naphthalen-1-yl)-carbamoyl]-methyl}-biphenyl-3-carboxylic acid methyl ester:

To a 0° C. solution of the product of preparation F (50 mg, 0.19 mmol) and methylene chloride (5 mL) was added oxalyl chloride (0.027 mL, 0.28 mmol) followed by DMF (1 drop). After stirring for 30 min, the reaction was concentrated and then toluene (3×10 mL) was added and then removed under vacuum. This acid chloride was then diluted with methylene chloride (2 mL) and added to a 0° C. solution of the product of preparation C (121 mg, 0.37 mmol), 4-dimethylaminopyridine (ca. 5 mg) and methylene chloride (2 mL). After 4 h, the reaction was concentrated and chromatographed on silica gel utilizing ethyl acetate/hexane as solvent to give the title compound (47%) isolated as an oil.

MS, APCI (%): 580 (M+1, 100).

Also prepared by this method were:

trans-3'-{[(2-Benzyl-1,2,3,4-tetrahydro-naphthalen-1-yl)-furan-2-ylmethyl-carbamoyl]-methyl}-biphenyl-3-carboxylic acid methyl ester:

MS, APCI (%): 570 (M+1, 100), 350 (15).

trans-3'-{[(2-Benzyl-1,2,3,4-tetrahydro-naphthalen-1-yl)-furan-3-ylmethyl-carbamoyl]-methyl}-biphenyl-3-carboxylic acid methyl ester:

MS, APCI (%): 570 (M+1, 100), 350 (30).

trans-3'-{[(2-Benzyl-1,2,3,4-tetrahydro-naphthalen-1-yl)-isoxazol-5-ylmethyl-carbamoyl]-methyl}-biphenyl-3-carboxylic acid methyl ester:

MS, APCI (%): 571 (M+1, 100), 351 (10).

Example 1 trans-3'-{[Benzyl-(2-benzyl-1,2,3,4-tetrahydro-naphthalen-1-yl)-carbamoyl]-methyl}-biphenyl-3-carboxylic acid:

A solution of the product of preparation G (50 mg, 0.086 mmol), water (1 mL), methanol (5 mL) and lithium hydroxide (4 mg, 0.17 mmol) was heated to reflux for 3 h and then allowed to cool. The reaction mixture was concentrated and then 0.1 N HCl was added until pH 1. This was then diluted with water and extracted with ethyl acetate three times. The combined organic layers were washed with brine, dried (sodium sulfate), and concentrated. The title compound was isolated in 62% yield as a white solid following trituration with ethyl acetate/hexane, mp 171–172° C.

MS, APCI (%): 564 (M−1, 100).

Also prepared by this method were:

trans-2'-{[Benzyl-(2-benzyl-1,2,3,4-tetrahydro-naphthalen-1-yl)-carbamoyl]-methyl}-biphenyl-2-carboxylic acid:

MS, APCI (%): 564 (M−1, 70).

trans-2'-{[Benzyl-(2-benzyl-1,2,3,4-tetrahydro-naphthalen-1-yl)-carbamoyl]-methyl}-biphenyl-3-carboxylic acid:

MS, APCI (%): 566 (M+1, 100).

trans-2'-{[Benzyl-(2-benzyl-1,2,3,4-tetrahydro-naphthalen-1-yl)-carbamoyl]-methyl}-biphenyl-4-carboxylic acid:

MS, APCI (%): 566 (M+1, 100), 346 (40).

trans-3'-{[Benzyl-(2-benzyl-1,2,3,4-tetrahydro-naphthalen-1-yl)-carbamoyl]-methyl}-biphenyl-2-carboxylic acid:

MS, APCI (%): 566 (M+1, 60), 328 (90), 221 (100).

trans-3'-{[Benzyl-(2-benzyl-1,2,3,4-tetrahydro-naphthalen-1-yl)-carbamoyl]-methyl}-biphenyl-4-carboxylic acid:

MS, APCI (%): 566 (M+1, 100).

trans-4'-{[Benzyl-(2-benzyl-1,2,3,4-tetrahydro-naphthalen-1-yl)-carbamoyl]-methyl}-biphenyl-2-carboxylic acid:

MS, APCI (%): 564 (M−1, 100).

trans-4'-{[Benzyl-(2-benzyl-1,2,3,4-tetrahydro-naphthalen-1-yl)-carbamoyl]-methyl}-biphenyl-3-carboxylic acid:

MS, APCI (%): 566 (M+1, 100), 269 (80), 187 (60).

trans-4'-{[Benzyl-(2-benzyl-1,2,3,4-tetrahydro-naphthalen-1-yl)-carbamoyl]-methyl}-biphenyl-4-carboxylic acid:

MS, APCI (%): 566 (M+1, 100).

trans-6-(3-{[Benzyl-(2-benzyl-1,2,3,4-tetrahydro-naphthalen-1-yl)-carbamoyl]-methyl}-phenyl)-pyridine-2-carboxylic acid:

MS, APCI (%): 566 (M+1, 100), 523 (50).

trans-3'-{[(2-Benzyl-1,2,3,4-tetrahydro-naphthalen-1-yl)-furan-2-ylmethyl-carbamoyl]-methyl}-biphenyl-3-carboxylic acid:

MS, APCI (%): 556 (M+1, 100).

trans-3'-{[(2-Benzyl-1,2,3,4-tetrahydro-naphthalen-1-yl)-furan-3-ylmethyl-carbamoyl]-methyl}-biphenyl-3-carboxylic acid:

MS, APCI (%): 556 (M+1, 100).

trans-3'-{[(2-Benzyl-1,2,3,4-tetrahydro-naphthalen-1-yl)-isoxazol-5-ylmethyl-carbamoyl]-methyl}-biphenyl-3-carboxylic acid:

MS, APCI (%): 557 (M+1, 100).

trans-3'-({Benzyl-[2-(3-methoxy-benzyl)-1,2,3,4-tetrahydro-naphthalen-1-yl]-carbamoyl}-methyl)-biphenyl-3-carboxylic acid:

MS, APCI (%): 596 (M+1, 100).

trans-3'-{[Benzyl-(2-benzyl-6-methoxy-1,2,3,4-tetrahydro-naphthalen-1-yl)-carbamoyl]-methyl}-biphenyl-3-carboxylic acid:

MS, APCI (%): 596 (M+1, 100).

Example 2 trans-N-Benzyl-N-(2-benzyl-1,2,3,4-tetrahydro-naphthalen-1-yl)-2-[3'-(4-fluoro-benzenesulfonylaminocarbonyl)-biphenyl-3-yl]-acetamide:

To a solution of the product of Example 1 (82.0 mg, 0.145 mmol), 4-fluorobenzene sulfonamide (27.9 mg, 0.160 mmol), bromo-tris-pyrrolidino-phosphonium hexafluoro-phosphate (PyBroP, 74.4 mg, 0.160 mmol), and methylene chloride (12 mL) was added diisopropylethyl amine (0.126 mL, 0.725 mmol). After stirring for 5 h, the reaction was concentrated to dryness and then diluted with ethyl acetate (25 mL). This was then washed with 0.1 N HCl (2×20 mL) and brine (25 mL), dried (magnesium sulfate), and concentrated. The title compound was isolated in quantitative yield as a foam following chromatography on silica gel with ethyl acetate/hexane.

MS, APCI (%): 723 (M+1, 80), 391 (35).

Also prepared by this method were:

trans-N-Benzyl-N-(2-benzyl-1,2,3,4-tetrahydro-naphthalen-1-yl)-2-(3'-methanesulfonylaminocarbonyl-biphenyl-3-yl)-acetamide:

MS, APCI (%): 643 (M+1, 100).

trans-N-Benzyl-N-(2-benzyl-1,2,3,4-tetrahydro-naphthalen-1-yl)-2-(3'-trifluoromethanesulfonylaminocarbonyl-biphenyl-3-yl)-acetamide:

MS, APCI (%): 695 (M−1, 100), 305 (95), 223 (95).

trans-N-Benzyl-N-(2-benzyl-1,2,3,4-tetrahydro-naphthalen-1-yl)-2-(3'-ethanesulfonylaminocarbonyl-biphenyl-3-yl)-acetamide:

MS, APCI (%): 657 (M+1, 100), 566 (60).

trans-N-Benzyl-N-(2-benzyl-1,2,3,4-tetrahydro-naphthalen-1-yl)-2-[3'-(3,4-difluoro-benzenesulfonylaminocarbonyl)-biphenyl-3-yl]-acetamide:

MS, APCI (%): 739 (M−1, 100), 563 (50), 541 (50), 323 (60).

trans-2-[(3'-{[Benzyl-(2-benzyl-1,2,3,4-tetrahydro-naphthalen-1-yl)-carbamoyl]-methyl}-biphenyl-3-carbonyl)-sulfamoyl]-benzoic acid methyl ester:

MS, APCI (%): 761 (M−1, 100), 563 (50), 345 (30).

Example 3 trans-2-[(3'-{[Benzyl-(2-benzyl-1,2,3,4-tetrahydro-naphthalen-1-yl)-carbamoyl]-methyl}-biphenyl-3-carbonyl)-sulfamoyl]-benzoic acid:

To a solution of the product of Example 2 (61.3 mg, 0.080 mmol) and methanol (1.5 mL) was added 1 N NaOH (0.45 mL, 0.45 mmol). After heating to reflux for 16 h, the reaction was concentrated to dryness and partitioned between ethyl acetate (10 mL) and 0.1 N HCl (10 mL). The organic layer was removed, dried (magnesium sulfate), and concentrated. The title compound was isolated as a foam following chromatography on silica gel with ethyl acetate/acetic acid.

MS, APCI (%): 749 (M+1, 100), 565 (30).

Preparation H trans-[(3'-{[Benzyl-(2-benzyl-1,2,3,4-tetrahydro-naphthalen-1-yl)-carbamoyl]-methyl}-biphenyl-3-carbonyl)-amino]-acetic acid tert-butyl ester:

In a procedure similar to example 2, the title compound was prepared in 75% and isolated as a foam following chromatography on silica gel with ethyl acetate/hexane.

MS, APCI (%): 679 (M+1, 50), 623 (100).

Example 4 trans-[(3'-{[Benzyl-(2-benzyl-1,2,3,4-tetrahydro-naphthalen-1-yl)-carbamoyl]-methyl}-biphenyl-3-carbonyl)-amino]-acetic acid To a solution of the product of preparation H (90 mg, 0.13 mmol) and methylene chloride (15 mL) was added trifluoroacetic acid (5 mL). The reaction was allowed to stir at room temperature for 3 h, concentrated and then triturated with ethyl acetate/hexane to give the title compound, which was isolated as a foam, in 74% yield.

MS, APCI (%): 621 (M−1, 100), 401 (60).

Preparation I

1-Benzylamino-2-benzylcyclohexane

In a series of procedures similar to preparations A and B, 2-benzyl cyclohexanone was converted into 1-amino-2-benzylcyclohexane in 65% via the intermediate oxime. This material (3.05 g, 16.1 mmol) was then converted to the title compounds in a procedure similar to preparation C, isolated as an oil:

trans isomer (2.05 g, 46% yield):

$^1$H-NMR (CDCl$_3$, δ): 0.8–2.3 (multiplets, 11H), 3.24 (dd, J=4.0, 13 Hz, 1H), 4.72 (d, J=13 Hz, 1H), 4.94 (d, J=13 Hz, 1H), 7.1–7.5 (m, 10H).

MS, APCI (%): 280 (M+1, 100).

cis isomer (0.28 g, 6% yield):

$^1$H-NMR (CDCl$_3$, δ): 1.0–2.0 (multiplets, 9H), 2.51 (dd, J=9.1, 13 Hz, 1H), 2.70 (dd, J=3.2, 6.5 Hz, 1H), 2.80 (dd, J=6.5, 13 Hz, 1H), 3.68 (d, J=13 Hz, 1H), 3.81 (d, J=13 Hz, 1H), 7.1–7.5 (m, 10H).

MS, APCI (%): 280 (M+1, 100).

Preparation J trans-3'-{[Benzyl-(2-benzyl-cyclohexyl)-carbamoyl]-methyl}-biphenyl-3-carboxylic acid methyl ester:

In a procedure similar to example 2, and utilizing the products of preparations F and I as starting materials, the title compound was prepared in 56% yield and isolated as a foam following chromatography on silica gel with ethyl acetate/hexane.

MS, APCI (%): 532 (M+1, 100).

Preparation K cis-3'-{[Benzyl-(2-benzyl-cyclohexyl)-carbamoyl]-methyl}-biphenyl-3-carboxylic acid methyl ester:

In a procedure similar to example 2, and utilizing the products of preparations F and I as starting materials, the title compound was prepared in 20% yield and isolated as a foam following chromatography on silica gel with ethyl acetate/hexane.

MS, APCI (%): 532 (M+1, 100), 509 (20), 477 (20).

Example 5 trans-3'-{[Benzyl-(2-benzyl-cyclohexyl)-carbamoyl]-methyl}-biphenyl-3-carboxylic acid:

In a procedure similar to Example 3, the product of preparation I afforded the title compound, isolated as a foam, in 95% yield.

MS, APCI (%): 518 (M+1, 100).

Example 6 cis-3'-{[Benzyl-(2-benzyl-cyclohexyl)-carbamoyl]-methyl}-biphenyl-3-carboxylic acid:

In a procedure similar to Example 3, the product of preparation K afforded the title compound, isolated as a foam, in 50% yield.

MS, APCI (%): 518 (M+1, 100).

Example 7 cis-2-[(3'-{[Benzyl-(2-benzyl-cyclohexyl)-carbamoyl]-methyl}-biphenyl-3-carbonyl)-sulfamoyl]-benzoic acid methyl ester:

In a procedure similar to Example 2, utilizing the product of example 6, the title compound was isolated as an oil in 54% following chromatography on silica gel with ethyl acetate/hexanes.

MS, APCI (%): 715 (M+1, 60), 515 (50), 199 (100).

Example 8 cis-2-[(3'-{[Benzyl-(2-benzyl-cyclohexyl)-carbamoyl]-methyl}-biphenyl-3-carbonyl)-sulfamoyl]-benzoic acid:

In a procedure similar to Example 3, utilizing the product of Example 7, the title compound was isolated as an foam in 84% yield.

MS, APCI (%): 701 (M+1, 100).

Preparation L (2-Benzyl-1,2,3,4-tetrahydro-naphthalen-1-yl)-isopropyl-amine:

In a procedure similar to preparation C, the title compound was isolated as an oil following chromatography on silica gel with ethyl acetate/hexanes.

Less polar diastereomer, assigned cis stereochemistry (18%).

¹H-NMR (CDCl₃, δ): 1.05 (d, J=6.2 Hz, 6H), 1.6 (m, 2H), 2.1 (m, 1H), 2.7 (m, 2H), 2.9 (m, 2H), 3.03 (app pent, J=6.2 Hz, 1H), 3.68 (d, J=3.5 Hz, 1H), 7.0–7.4 (m, 9H).

MS, APCI (%): 280 (M+1, 100), 221 (90).

More polar trans diastereomer, (15%).

¹H-NMR (CDCl₃, δ): 0.96, 0.99 (d, J=6.1 Hz, 6H), 1.6 (m, 1H), 2.10 (m, 1H), 2.25 (m, 1H), 2.47 (dd, J=8.3, 14Hz, 1H), 2.58 (dd, J=7.6, 14Hz, 1H), 2.70 (ddd, J=3.1, 6.6, 17Hz, 1H), 2.81 (ddd, J=6.0, 11, 17Hz, 1H) 2.92 (hept, J=6.2 Hz, 1H), 3.52 (d, J=2.5 Hz, 1H), 7.0–7.4 (m, 9H).

MS, APCI (%): 280 (M+1, 100), 221 (90).

Preparation M trans-3'-{[(2-Benzyl-1,2,3,4-tetrahydro-naphthalen-1-yl)-isopropyl-carbamoyl]-methyl}-biphenyl-3-carboxylic acid methyl ester:

In a procedure similar to example 2, the products of preparations L and F were reacted to give the title compound, isolated as an oil in 48% yield, following chromatography on silica gel with methylene chloride.

MS, APCI (%): 532 (M+1, 100), 312 (20).

Preparation N cis-3'-{[(2-Benzyl-1,2,3,4-tetrahydro-naphthalen-1-yl)-isopropyl-carbamoyl]-methyl}-biphenyl-3-carboxylic acid methyl ester:

In a procedure similar to example 2, the products of preparations L and F were reacted to give the title compound, isolated as an oil in 7% yield, following chromatography on silica gel with methylene chloride.

MS, APCI (%): 532 (M+1, 100), 312 (50).

Example 9 cis-3'-{[(2-Benzyl-1,2,3,4-tetrahydro-naphthalen-1-yl)-isopropyl-carbamoyl]-methyl}-biphenyl-3-carboxylic acid:

In a procedure similar to example 1, utilizing the product of preparation N, the title compound was isolated as an oil in 75% yield.

MS, APCI (%): 518 (M+1, 100), 298 (30).

Example 10 trans-3'-{[(2-Benzyl-1,2,3,4-tetrahydro-naphthalen-1-yl)-isopropyl-carbamoyl]-methyl}-biphenyl-3-carboxylic acid:

In a procedure similar to example 1, utilizing the product of preparation N, the title compound was isolated as an oil in 77% yield.

¹H-NMR (CDCl₃, δ): 1.24, 1.26, 1.56 (d, J=6.2 Hz, 6H), 1.4 (m, 2H), 1.9 (m, 1H), 2.1 (m, 1H), 2.7 (m, 2H), 2.9 (m, 2H), 3.07 (app pent, J=6.4 Hz, 1H), 3.14 (d, J=13 Hz, 1H), 3.86 (d, J=15 Hz, 1H), 3.95 (d, J=15 Hz, 1H), 4.92 (d, J=9.2 Hz, 1H), 6.94 (d, J=7.7 Hz, 1H) 7.0–7.6 (m, 13H), 7.75 (d, J=7.3 Hz, 1H), 8.03 (d, J=7.9 Hz, 1H), 8.26 (s, 1H).

MS, APCI (%): 518 (M+1, 100), 298 (40).

Preparation O

1-Methylamino-2-benzylcyclohexane:

To a solution of 1-amino-2-benzylcyclohexane (an intermediate in preparation I, 0.90 gm, 4.8 mmol) and methanol (25 mL) was added RhH(Ph₃P)₃ (275 mg, 0.24 mmol) and the reaction mixture heated to reflux for 12 h. After cooling to room temperature, the solvent was removed under vacuum and the residue chromatographed on neutral alumina with ether and then on silica gel with triethylamine/ethyl acetate/hexane to give the title compound isolated as an oil in 14% yield.

MS, APCI (%): 204 (M+1, 100).

Preparation P

3'-{[(2-Benzyl-cyclohexyl)-methyl-carbamoyl]-methyl}-biphenyl-3-carboxylic acid methyl ester:

In a procedure similar to example 2, the products of preparations O and F were reacted to give the title compound, isolated as an oil in 29% yield, following chromatography on silica gel with ethyl acetate/hexane.

MS, APCI (%): 456 (M+1, 100).

Example 11

3'-{[(2-Benzyl-cyclohexyl)-methyl-carbamoyl]-methyl}-biphenyl-3-carboxylic acid:

In a procedure similar to example 1, utilizing the product of preparation P, the title compound was isolated as an foam in quantitative yield.

MS, APCI (%): 441 (M+1, 100).

Preparation Q trans-4-[(2-Benzyl-1,2,3,4-tetrahydro-naphthalen-1-ylamino)-methyl]-benzoic acid methyl ester:

In a procedure similar to preparation C, the title compound was prepared from 1-amino-2-benzyltetralin and 4-carbomethoxybenzaldehyde. The trans isomer was isolated as an oil in 20% yield following chromatography on silica gel with ethyl acetate/hexane.

¹H-NMR (CDCl₃, δ): 1.6 (m, 2H), 2.10 (m, 1H), 2.3 (m, 1H), 2.51 (dd, J=7.8, 14 Hz, 1H), 2.67 (dd, J=7.3, 14 Hz, 1H), 2.8 (m, 2H), 3.56 (d, J=4.2 Hz, 1H), 3.78 (d, J=14 Hz, 1H), 3.78 (d, J=14 Hz, 1H), 7.1–7.3 (m, 11H), 7.93 (d, J=8.5, 1H).

MS, APCI (%): 386 (M+1, 100), 221 (30).

Preparation R trans-3-[(2-Benzyl-1,2,3,4-tetrahydro-naphthalen-1-ylamino)-methyl]-benzoic acid methyl ester:

In a procedure similar to preparation C, the title compound was prepared from 1-amino-2-benzyltetralin and 3-carbomethoxybenzaldehyde. The trans isomer was isolated as an oil in 28% yield following chromatography on silica gel with ethyl acetate/hexane.

¹H-NMR (CDCl₃, δ): 1.6 (m, 2H), 2.10 (m, 1H), 2.3 (m, 1H), 2.45 (dd, J=8.2, 14 Hz, 1H), 2.70 (dd, J=7.0, 14 Hz, 1H), 2.8 (m, 2H), 3.59 (d, J=4.2 Hz, 1H), 3.73 (d, J=13 Hz, 1H), 3.78 (d, J=13 Hz, 1H), 7.1–7.3 (m, 9H), 7.34 (t, J=7.7 Hz, 1H), 7.43 (d, J=7.7 Hz, 1H), 7.89 (dt, J=1.5, 7.7 Hz, 1H), 7.93 (t, J=1.5, 1H).

MS, APCI (%): 386 (M+1, 100), 221 (20).

Preparation S trans-3'-{[(2-Benzyl-1,2,3,4-tetrahydro-naphthalen-1-yl)-(4-methoxycarbonyl-benzyl)-carbamoyl]-methyl}-biphenyl-3-carboxylic acid methyl ester:

In a procedure similar to example 2, the products of preparations Q and F were reacted to give the title compound, isolated as an foam in 48% yield, following chromatography on silica gel with ethyl acetate/hexane.

MS, APCI (%): 638 (M+1, 100).

Preparation T trans-3'-{[(2-Benzyl-1,2,3,4-tetrahydro-naphthalen-1-yl)-(3-methoxycarbonyl-benzyl)-carbamoyl]-methyl}-biphenyl-3-carboxylic acid methyl ester:

In a procedure similar to example 2, the products of preparations R and F were reacted to give the title compound, isolated as an foam in 53% yield, following chromatography on silica gel with ethyl acetate/hexane.

MS, APCI (%): 638 (M+1, 100).

Example 12 trans-3'-{[(2-Benzyl-1,2,3,4-tetrahydro-naphthalen-1-yl)-(4-carboxy-benzyl)-carbamoyl]-methyl}-biphenyl-3-carboxylic acid:

In a procedure similar to example 1, utilizing the product of preparation S, the title compound was isolated as an foam in 95% yield.

MS, APCI (%): 610 (M+1, 100), 250 (30).

Example 13 trans-3'-{[(2-Benzyl-1,2,3,4-tetrahydro-naphthalen-1-yl)-(3-carboxy-benzyl)-carbamoyl]-methyl}-biphenyl-3-carboxylic acid:

In a procedure similar to example 1, utilizing the product of preparation T, the title compound was isolated as an foam in 91% yield.

MS, APCI (%): 610 (M+1, 100), 515 (55).

Preparation U

2'-tert-Butoxycarbonylmethyl-biphenyl-2-carboxylic acid methyl ester:

To a solution of (2-bromo-phenyl)-acetic acid tert-butyl ester (678 mg, 2.5 mmol), bis(pinacolato)diboron (698 mg, 2.75 mmol), potassium acetate (736 mg, 7.5 mmol) and DMF (15 mL) was added $PdCl_2$(dppf) (61 mg, 0.75 mmol). After evacuating and refilling with nitrogen three times, the reaction was heated to 80° C. for 2 h. After cooling to room temperature, methyl 2-bromo-benzoate (1.08 g, 5.0 mmol), 2M $Na_2CO_3$ aqueous (6.25 mL) and $PdCl_2$(dppf) (61 mg, 0.75 mmol) was added to the reaction.). After evacuating and refilling with nitrogen three times again, the reaction was heated to 80° C. for 14 h. After cooling to room temperature, the mixture was poured into water (15 mL) and extracted with ether (3×25 mL). The combined organic layers were washed with water (3×25 mL), brine, dried (magnesium sulfate), and concentrated. The title compound was isolated in 22% yield as an oil following chromatography on silica gel utilizing ethyl acetate/hexane as solvent.

$^1$H-NMR ($CDCl_3$, δ): 1.34 (s, 9H), 3.27 (d, J=16 Hz, 1H), 3.34 (d, J=16 Hz, 1H), 3.57 (s, 3H), 7.08 (d, J=7.3 Hz, 1H), 7.2–7.35 (m, 5H), 7.42 (dt, J=1.5, 7.7 Hz, 1H), 7.50 (dt, J=1.5, 7.7 Hz, 1H).

Also prepared by this method were:

3'-tert-Butoxycarbonylmethyl-biphenyl-2-carboxylic acid methyl ester:

$^1$H-NMR ($CDCl_3$, δ): 1.43 (s, 9H), 3.55 (s, 2H), 3.61 (s, 3H), 7.2 (m, 2H), 7.29 (d, J=7.5 Hz, 1H), 7.35 (m, 3H), 7.50 (dt, J=1.5, 7.5 Hz, 1H), 7.80 (dd, J=1.5, 7.7 Hz, 1H).

4'-tert-Butoxycarbonylmethyl-biphenyl-2-carboxylic acid methyl ester:

$^1$H-NMR ($CDCl_3$, δ): 1.44 (s, 9H), 3.56 (s, 2H), 3.62 (s, 3H), 7.25 (m, 4H), 7.38 (dq, J=1.5, 7.7 Hz, 1H), 7.51 (dt, J=1.5, 7.7 Hz, 1H), 7.80 (dd, J=1.5, 7.7 Hz, 1H).

6-(3-tert-Butoxycarbonylmethyl-phenyl)-pyridine-2-carboxylic acid methyl ester:

$^1$H-NMR ($CDCl_3$, δ): 1.43 (s, 9H), 3.62 (s, 2H), 4.01 (s, 3H), 7.35 (dq, J=1.2, 7.7 Hz, 1H), 7.43 (t, J=7.7 Hz, 1H), 7.85–7.95 (m, 4H), 8.05 (dd, J=3.8, 4.8 Hz, 1H).

Preparation V trans-2'-{[Benzyl-(2-benzyl-1,2,3,4-tetrahydro-naphthalen-1-yl)-carbamoyl]-methyl}-biphenyl-2-carboxylic acid methyl ester:

To a solution of the product of preparation C (62 m, 0.19 mmol), 2'-carboxymethyl-biphenyl-2-carboxylic acid methyl ester (61 mg, 0.23 mmol), dichloroethane (10 ml), and diisopropyl ethylamine (79 µL, 0.46 mmol) was added PyBrop (106 mg, 0.23 mmol) and the solution allowed to stir overnight. The reaction was concentrated to dryness, diluted with ethyl acetate and then washed sequentially with 0.1 N HCl (3×), 5% sodium bicarbonate (3×) and brine (2×). The solution was dried (MgSO4) and concentrated and the chromatographed to give the title compound (52% yield), isolated as an oil.

MS, APCI (%): 580 (M+1, 100), 602 (M+Na, 40).

Also prepared by this method were:

trans-2'-{[Benzyl-(2-benzyl-1,2,3,4-tetrahydro-naphthalen-1-yl)-carbamoyl]-methyl}-biphenyl-3-carboxylic acid methyl ester:

MS, APCI (%): 580 (M+1, 100), 360 (40).

trans-2'-{[Benzyl-(2-benzyl-1,2,3,4-tetrahydro-naphthalen-1-yl)-carbamoyl]-methyl}-biphenyl-4-carboxylic acid methyl ester:

MS, APCI (%): 580 (M+1, 100), 360 (80).

trans-3'-{[Benzyl-(2-benzyl-1,2,3,4-tetrahydro-naphthalen-1-yl)-carbamoyl]-methyl}-biphenyl-2-carboxylic acid methyl ester:

MS, APCI (%): 580 (M+1, 100) 602 (M+Na, 50).

trans-3'-{[Benzyl-(2-benzyl-1,2,3,4-tetrahydro-naphthalen-1-yl)-carbamoyl]-methyl}-biphenyl-4-carboxylic acid methyl ester:

MS, APCI (%): 580 (M+1, 100), 360 (10).

trans-4'-{[Benzyl-(2-benzyl-1,2,3,4-tetrahydro-naphthalen-1-yl)-carbamoyl]-methyl}-biphenyl-2-carboxylic acid methyl ester:

MS, APCI (%): 580 (M+1, 100) 602 (M+Na, 60).

trans-4'-{[Benzyl-(2-benzyl-1,2,3,4-tetrahydro-naphthalen-1-yl)-carbamoyl]-methyl}-biphenyl-3-carboxylic acid methyl ester:

MS, APCI (%): 580 (M+1, 100) 360 (40).

trans-4'-{[Benzyl-(2-benzyl-1,2,3,4-tetrahydro-naphthalen-1-yl)-carbamoyl]-methyl}-biphenyl-4-carboxylic acid methyl ester:

MS, APCI (%): 580 (M+1, 100) 490 (20), 360 (10).

6-(3-{[Benzyl-(2-benzyl-1,2,3,4-tetrahydro-naphthalen-1-yl)-carbamoyl]-methyl}-phenyl)-pyridine-2-carboxylic acid methyl ester:

MS, APCI (%): 581 (M+1, 100) 603 (M+Na, 80), 364 (30).

Preparation W

(2-Benzyl-1,2,3,4-tetrahydro-naphthalen-1-yl)-isoxazol-5-ylmethyl-amine:

To a mixture of the product of preparation B (1.8 g, 7.6 mmol), sodium carbonate (804 mg, 7.6 mmol) and acetonitrile (50 mL) was added isoxazol-5-ylmethyl iodide (1.6 g, 7.6 mmol) and the reaction mixture was then heated at reflux for 6 h. After cooling to room temperature, the solvent was removed under vacuum, and the residue partitioned between water and ethyl acetate. The organic layer solution was washed with water (50 mL), brine, dried ($Na_2SO_4$), and concentrated to give an oil. Chromatography on silica gel utilizing ethyl acetate/hexanes gave the separated isomers:

Less polar diastereomer, assigned cis stereochemistry (58%):

$^1$H-NMR ($CDCl_3$, δ): 1.8 (m, 2H), 2.2 (m, 1H), 2.75 (dd, J=8.3, 14 Hz, 1H), 2.82 (dd, J=8.9, 14 Hz, 1H), 2.9 (m, 2H), 3.50 (d, J=3.4 Hz), 3.85 (d, J=15 Hz, 1H), 4.03 (d, J=15 Hz, 1H), 6.15 (d, J=2.2 Hz, 1H), 7.0–7.4 (m, 9H), 8.18 (d, J=2.2 Hz, 1H).

More polar diastereomer, assigned trans stereochemistry (9%):

$^1$H-NMR ($CDCl_3$, δ): 1.6 (m, 1H), 2.1 (m, 1H), 2.3 (m, 1H), 2.51 (dd, J=8.0, 13 Hz, 1H), 2.62 (dd, J=7.2, 13 Hz, 1H), 2.7 (m, 2H), 3.50 (d, J=3.4 Hz), 3.82 (s, 2H), 6.15 (d, J=2.0 Hz, 1H), 7.0–7.3 (m, 13H), 8.12 (d, J=2.0 Hz, 1H).

Preparation X

3'-({Benzyl-[2-(3-methoxy-benzyl)-1,2,3,4-tetrahydro-naphthalen-1-yl]-carbamoyl}-methyl)-biphenyl-3-carboxylic acid methyl ester:

3'-Carboxymethyl-biphenyl-3-carboxylic acid methyl ester (77 mg) is combined with 76 mg 1-hydroxy-7-azabenzotriazole, 234 mg polymer-bound DCC, and 4 mg 4-dimethylaminopyridine in 4 ml 3:1 dichloroethane:DMF. The slurry is shaken 30 minutes at ambient temperature before adding 100 mg Benzyl-[2-(3-methoxy-benzyl)-1,2,3, 4-tetrahydro-naphthalen-1-yl]-amine (prepared in a similar fashion to Preparation C). The mixture is shaken at ambient temperature 18 hours. The resin is filtered off and washed with dichloromethane and methanol. The solvent is evaporated to give a yellow oil. The oil is dissolved in dichloromethane, the insoluble material is filtered off, and the filtrate is separated by radial chromatography (4 mm plate, 3:1 hexanes:ethyl acetate). Product fractions are combined and evaporated to give 76 mg of the title compound as a colorless oil, 42%.

MS, APCI (%): 610.4 (M+1, 100%).

Also prepared by this method was:

3'-{[Benzyl-(2-benzyl-6-methoxy-1,2,3,4-tetrahydro-naphthalen-1-yl)-carbamoyl]-methyl}-biphenyl-3-carboxylic acid methyl ester.

What is claimed is:

1. A compound of the formula (II):

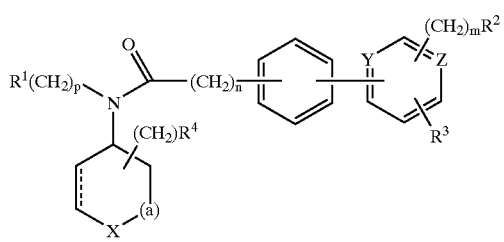

(II)

or pharmaceutically acceptable salts, hydrates and prodrugs thereof, wherein:

$R^1$ is H, $C_1$–$C_{10}$ alkyl, $C_2$–$C_{10}$ alkenyl, $C_2$–$C_{10}$ alkynyl, —$(CH_2)_t(C_6$–$C_{10}$ aryl), wherein t is an integer from 0 to 5; said alkyl group optionally including 1 or 2 hetero moieties selected from O, S and —N($R^6$)— with the proviso that two O atoms, two S atoms, or an O and S atom are not attached directly to each other; said aryl being optionally fused to a $C_6$–$C_{10}$ aryl group, or a $C_5$–$C_8$ saturated cyclic group, the —$(CH_2)_t$— moieties of $R^1$ optionally including a carbon-carbon double or triple bond when t is an integer from two to five; $R^1$ groups being optionally substituted by one to five $R^5$ groups;

each $R^5$ is independently selected from $C_1$–$C_{10}$ alkyl, $C_2$–$C_{10}$ alkenyl, $C_2$–$C_{10}$ alkynyl, halo, cyano, nitro, trifluoromethyl, trifluoromethoxy, azido, —$OR^6$, —$C(O)R^7$, —$C(O)OR^6$, —$NR^7C(O)OR^6$, —$OC(O)R^6$, —$NR^7SO_2R^6$, —$SO_2NR^6R^7$, —$NR^7C(O)R^6$, —$C(O)NR^6R^7$, —$NR^6R^7$, —$S(O)_jR^8$ wherein j is an integer ranging from zero to two, —$SO_3H$, —$NR^6(CR^7R^8)_tOR^7$, —$(CH_2)_t(C_6$–$C_{10}$ aryl), —$SO_2(CH_2)_t(C_6$–$C_{10}$ aryl), —$S(CH_2)_t(C_6$–$C_{10}$ aryl), —$O(CH_2)_t(C_6$–$C_{10}$ aryl), and —$(CR^7R^8)_mOR^7$, wherein m is an integer from one to five and t is an integer from zero to five; said alkyl group optionally containing one or two hetero moieties selected from O, S and —N($R^7$)— with the proviso that two O atoms, two S atoms, or an O and S atom are not attached directly to each other; aryl moieties of $R^5$ being optionally fused to a $C_6$–$C_{10}$ aryl group, a $C_5$–$C_8$ saturated cyclic group, and the alkyl, aryl moieties of $R^5$ groups being optionally substituted by one to three substituents independently selected from halo, cyano, nitro, trifluoromethyl, trifluoromethoxy, azido, —$NR^7SO_2R^6$, —$SO_2NR^6R^7$, —$C(O)R^6$, —$C(O)OR^6$, —$OC(O)R^6$, —$NR^7C(O)R^6$, —$C(O)NR^6R^7$, —$NR^6R^7$, —$(CR^7R^8)_mOR^7$ wherein m is an integer from one to five, —$OR^6$ and $R^6$;

each $R^6$ is independently selected from H, $C_1$–$C_{10}$ alkyl, —$(CH_2)_t(C_6$–$C_{10}$ aryl), wherein t is an integer from zero to five; said alkyl group optionally including one or two hetero moieties selected from O, S and —N($R^5$)— with the proviso that two O atoms, two S atoms, or an O and S atom are not attached directly to each other; said aryl $R^6$ groups being optionally fused to a $C_6$–$C_{10}$ aryl group, a $C_5$–$C_8$ saturated cyclic group, the foregoing moieties of $R^6$, with the exception of H, being optionally substituted by one to three substituents independently selected from halo, cyano, nitro, trifluoromethyl, trifluoromethoxy, azido, —$C(O)R^7$, —$C(O)OR^7$, —$CO(O)R^7$, —$NR^7C(O)R^8$, —$C(O)NR^7R^8$, —$NR^7R^8$, hydroxy, $C_1$–$C_6$ alkyl, and $C_1$–$C_6$ alkoxy;

each $R^7$ and $R^8$ is independently H or $C_1$–$C_6$ alkyl;

$R^2$ is a group having an acidic proton and is selected from the group consisting of —$CO_2H$, —$CONHSO_2R^1$, —$CONR^1(CH_2)CO_2H$, —$SO_2H$, —$PO_3H_2$;

each $R^3$ is independently selected from H and $R^2$;

$R^4$ is —$(CH_2)_t(C_6$–$C_{10}$ aryl), wherein t is an integer from zero to five; said alkyl group optionally including one or two hetero moieties selected from O, S and —$N(R^5)$— with the proviso that two O atoms, two S atoms, or an O and S atom are not attached directly to each other; said aryl $R^4$ groups are optionally fused to a $C_6$–$C_{10}$ aryl group, a $C_5$–$C_8$ saturated cyclic group; the —$(CH_2)_t$— moieties of $R^6$ optionally including a carbon-carbon double or triple bond where t is an integer from two to five, $R^4$ being optionally substituted by one to five $R^5$ groups;

Y and Z are independently CH;

m is zero or 1;

n is zero to 6;

p is zero to 6;

X is $CHR^1$;

a is 0, 1 or 2;

and the dotted line indicates optional fusion to a $C_6$–$C_{10}$ aryl group, a $C_5$–$C_8$ saturated cyclic group, each optionally substituted with one or more substituents selected from halogen, hydroxy, $C_1$–$C_{10}$ alkyl, $C_1$–$C_{10}$ alkoxy and methylenedioxy.

2. A compound of claim 1, selected from:

trans-3'-{[Benzyl-(2-benzyl-1,2,3,4-tetrahydro-naphthalen-1-yl)-carbamoyl]-methyl}-biphenyl-3-carboxylic acid;

trans-2'-{[Benzyl-(2-benzyl-1,2,3,4-tetrahydro-naphthalen-1-yl)-carbamoyl]-methyl}-biphenyl-2-carboxylic acid;

trans-2'-{[Benzyl-(2-benzyl-1,2,3,4-tetrahydro-naphthalen-1-yl)-carbamoyl]-methyl}-biphenyl-3-carboxylic acid;

trans-2'-{[Benzyl-(2-benzyl-1,2,3,4-tetrahydro-naphthalen-1-yl)-carbamoyl]-methyl}-biphenyl-4-carboxylic acid;

trans-3'-{[Benzyl-(2-benzyl-1,2,3,4-tetrahydro-naphthalen-1-yl)-carbamoyl]-methyl}-biphenyl-2-carboxylic acid;

trans-3'-{[Benzyl-(2-benzyl-1,2,3,4-tetrahydro-naphthalen-1-yl)-carbamoyl]-methyl}-biphenyl-4-carboxylic acid;

trans-4'-{[Benzyl-(2-benzyl-1,2,3,4-tetrahydro-naphthalen-1-yl)-carbamoyl]-methyl}-biphenyl-2-carboxylic acid;

trans-4'-{[Benzyl-(2-benzyl-1,2,3,4-tetrahydro-naphthalen-1-yl)-carbamoyl]-methyl}-biphenyl-3-carboxylic acid;

trans-4'-{[Benzyl-(2-benzyl-1,2,3,4-tetrahydro-naphthalen-1-yl)-carbamoyl]-methyl}-biphenyl-4-carboxylic acid;

trans-3'-({Benzyl-[2-(3-methoxy-benzyl)-1,2,3,4-tetrahydro-naphthalen-1-yl]-carbamoyl}-methyl)-biphenyl-3-carboxylic acid;

trans-3'-{[Benzyl-(2-benzyl-6-methoxy-1,2,3,4-tetrahydro-naphthalen-1-yl)-carbamoyl]-methyl}-biphenyl-3-carboxylic acid;

trans-N-Benzyl-N-(2-benzyl-1,2,3,4-tetrahydro-naphthalen-1-yl)-2-[3'-(4-fluoro-benzenesulfonylaminocarbonyl)-biphenyl-3-yl]-acetamide;

trans-N-Benzyl-N-(2-benzyl-1,2,3,4-tetrahydro-naphthalen-1-yl)-2-(3'-methanesulfonylaminocarbonyl-biphenyl-3-yl)-acetamide;

trans-N-Benzyl-N-(2-benzyl-1,2,3,4-tetrahydro-naphthalen-1-yl)-2-(3'-trifluoromethanesulfonylaminocarbonyl-biphenyl-3-yl)-acetamide;

trans-N-Benzyl-N-(2-benzyl-1,2,3,4-tetrahydro-naphthalen-1-yl)-2-(3'-ethanesulfonylaminocarbonyl-biphenyl-3-yl)-acetamide;

trans-N-Benzyl-N-(2-benzyl-1,2,3,4-tetrahydro-naphthalen-1-yl)-2-[3'-(3,4-difluoro-benzenesulfonylaminocarbonyl)-biphenyl-3-yl]-acetamide;

trans-2-[(3'-{[Benzyl-(2-benzyl-1,2,3,4-tetrahydro-naphthalen-1-yl)-carbamoyl]-methyl}-biphenyl-3-carbonyl)-sulfamoyl]-benzoic acid methyl ester;

trans-2-[(3'-{[Benzyl-(2-benzyl-1,2,3,4-tetrahydro-naphthalen-1-yl)-carbamoyl]-methyl}-biphenyl-3-carbonyl)-sulfamoyl]-benzoic acid;

trans-[(3'-{[Benzyl-(2-benzyl-1,2,3,4-tetrahydro-naphthalen-1-yl)-carbamoyl]-methyl}-biphenyl-3-carbonyl)-amino]-acetic acid;

trans-3'-{[Benzyl-(2-benzyl-cyclohexyl)-carbamoyl]-methyl}-biphenyl-3-carboxylic acid;

cis-3'-{[Benzyl-(2-benzyl-cyclohexyl)-carbamoyl]-methyl}-biphenyl-3-carboxylic acid;

cis-2-[(3'-{[Benzyl-(2-benzyl-cyclohexyl)-carbamoyl]-methyl}-biphenyl-3-carbonyl)-sulfamoyl]-benzoic acid methyl ester;

cis-2-[(3'-{[Benzyl-(2-benzyl-cyclohexyl)-carbamoyl]-methyl}-biphenyl-3-carbonyl)-sulfamoyl]-benzoic acid;

cis-3'-{[(2-Benzyl-1,2,3,4-tetrahydro-naphthalen-1-yl)-isopropyl-carbamoyl]-methyl}-biphenyl-3-carboxylic acid;

trans-3'-{[(2-Benzyl-1,2,3,4-tetrahydro-naphthalen-1-yl)-isopropyl-carbamoyl]-methyl}-biphenyl-3-carboxylic acid;

3'-{[(2-Benzyl-cyclohexyl)-methyl-carbamoyl]-methyl}-biphenyl-3-carboxylic acid;

trans-3'-{[(2-Benzyl-1,2,3,4-tetrahydro-naphthalen-1-yl)-(4-carboxy-benzyl)-carbamoyl]-methyl}-biphenyl-3-carboxylic acid;

trans-3'-{[(2-Benzyl-1,2,3,4-tetrahydro-naphthalen-1-yl)-(3-carboxy-benzyl)-carbamoyl]-methyl}-biphenyl-3-carboxylic acid.

3. A compound of claim 1, wherein $R^1$ is H, $C_1$–$C_{10}$ alkyl, $C_2$–$C_{10}$ alkenyl, $C_2$–$C_{10}$ alkynyl, $C_6$–$C_{10}$ aryl, wherein any aromatic carbocyclic rings are optionally substituted with one or more substituents selected from halogen, hydroxy, $C_1$–$C_6$alkoxy, $C_1$–$C_6$alkyl, $CF_3$, $CO_2H$, $CO_2$alkyl or CN.

4. A compound of claim 1, wherein $R^4$ is phenyl optionally substituted with one or more substituents selected from halogen, hydroxy, $C_1$–$C_6$alkoxy, $C_1$–$C_6$alkyl, or methylenedioxy.

5. The compound of claim 1, wherein (a) is 1.

6. A pharmaceutical composition for the treatment of a hyperproliferative disorder in a mammal which comprises a therapeutically effective amount of a compound of claim 1 and a pharmaceutically acceptable carrier.

* * * * *